(12) United States Patent
Merritt et al.

(10) Patent No.: US 10,098,702 B2
(45) Date of Patent: Oct. 16, 2018

(54) DEVICES, SYSTEMS, AND METHODS FOR TREATMENT OF VESSELS

(71) Applicants: Fergus Merritt, Escondido, CA (US); Justin Davies, London (GB)

(72) Inventors: Fergus Merritt, Escondido, CA (US); Justin Davies, London (GB)

(73) Assignee: VOLCANO CORPORATION, San Diego, CA (US)

( * ) Notice: Subject to any disclaimer, the term of this patent is extended or adjusted under 35 U.S.C. 154(b) by 251 days.

(21) Appl. No.: 14/796,719

(22) Filed: Jul. 10, 2015

(65) Prior Publication Data

US 2016/0008084 A1 Jan. 14, 2016

Related U.S. Application Data

(60) Provisional application No. 62/023,296, filed on Jul. 11, 2014.

(51) Int. Cl.
*A61B 5/05* (2006.01)
*A61B 19/00* (2006.01)
(Continued)

(52) U.S. Cl.
CPC ............ *A61B 19/50* (2013.01); *A61B 5/0066* (2013.01); *A61B 5/02158* (2013.01); *A61B 5/06* (2013.01);
(Continued)

(58) Field of Classification Search
CPC combination set(s) only.
See application file for complete search history.

(56) References Cited

U.S. PATENT DOCUMENTS 6,200,268 B1 4/2001 Vince et al.
6,381,350 B1 4/2002 Klingensmith et al.
(Continued)

FOREIGN PATENT DOCUMENTS

| WO | WO2000/53081 | 9/2000 |
|---|---|---|
| WO | WO2013/028612 | 2/2013 |
| WO | WO2014/106186 | 7/2014 |

OTHER PUBLICATIONS

International Preliminary Report on Patentability for PCT/US2012/051566, dated Feb. 25, 2014, International Search Report and Written Opinion received in Patent Cooperation Treaty Application No. PCT/US2012/051566, dated Feb. 25, 2014, 10 pages.
(Continued)

*Primary Examiner* — Joel F Brutus

(57) ABSTRACT

Devices, systems, and methods configured to assess the severity of a blockage in a vessel and, in particular, a stenosis in a blood vessel, provide visual depictions of vessel that allow assessment of the vessel and, in particular, any stenosis or lesion of the vessel, simulate one or more treatment options for the vessel, and perform treatment on any stenosis or lesion of the vessel, including guiding placement of one or more treatment devices are provided. The method can include obtaining pressure measurements from first and second instruments positioned within a vessel of a patient during a diagnostic procedure where the second instrument is moved longitudinally through the vessel; identifying a treatment option based on the obtained pressure measurements; and performing the identified treatment option, wherein a user display guides placement of one or more treatment devices associated with the identified treatment option.

28 Claims, 21 Drawing Sheets

(51) Int. Cl.
*A61B 5/00* (2006.01)
*A61B 6/03* (2006.01)
*A61B 8/12* (2006.01)
*A61B 5/0215* (2006.01)
*A61B 5/06* (2006.01)
*A61B 34/10* (2016.01)

(52) U.S. Cl.
CPC ............ *A61B 5/4848* (2013.01); *A61B 5/685* (2013.01); *A61B 5/6851* (2013.01); *A61B 5/6862* (2013.01); *A61B 5/6876* (2013.01); *A61B 5/7425* (2013.01); *A61B 6/03* (2013.01); *A61B 8/12* (2013.01); *A61B 34/10* (2016.02); *A61B 2034/107* (2016.02); *A61B 2562/0247* (2013.01)

(56) References Cited

U.S. PATENT DOCUMENTS

| | | | |
|---|---|---|---|
| 7,074,188 | B2 | 7/2006 | Nair et al. |
| 7,175,597 | B2 | 2/2007 | Vince et al. |
| 7,215,802 | B2 | 5/2007 | Klingensmith et al. |
| 7,359,554 | B2 | 4/2008 | Klingensmith et al. |
| 7,463,759 | B2 | 12/2008 | Klingensmith et al. |
| 7,930,014 | B2 | 4/2011 | Huennekens |
| 2002/0115931 | A1 | 8/2002 | Strauss et al. |
| 2006/0052700 | A1 | 3/2006 | Svanerudh |
| 2006/0106321 | A1 | 5/2006 | Lewinsky et al. |
| 2006/0241465 | A1 | 10/2006 | Huennekens |
| 2007/0038061 | A1 | 2/2007 | Huennekens et al. |
| 2007/0038081 | A1 | 2/2007 | Eck et al. |
| 2007/0060822 | A1 | 3/2007 | Alpert et al. |
| 2010/0234698 | A1 | 9/2010 | Manstrom |
| 2010/0268067 | A1* | 10/2010 | Razzaque ............ A61B 8/4245 600/424 |
| 2011/0075912 | A1 | 3/2011 | Rieber et al. |
| 2011/0142318 | A1* | 6/2011 | Chen ................... G06K 9/4614 382/131 |
| 2012/0087562 | A1* | 4/2012 | Isaacs .................. G06F 19/321 382/131 |
| 2013/0046190 | A1 | 2/2013 | Davies et al. |
| 2013/0345574 | A1 | 12/2013 | Davies et al. |
| 2014/0094697 | A1* | 4/2014 | Petroff ................ A61B 5/0066 600/427 |
| 2014/0187920 | A1* | 7/2014 | Millett ................. A61B 6/5247 600/424 |
| 2015/0025330 | A1 | 1/2015 | Davies et al. |

OTHER PUBLICATIONS

International Preliminary Report on Patentability for PCT/US2013/078321, dated Jun. 30, 2015, International Search Report and Written Opinion received in Patent Cooperation Treaty Application No. PCT/US2013/078321, dated Apr. 24, 2014, 11 pages.

* cited by examiner

DEVICES, SYSTEMS, AND METHODS FOR TREATMENT OF VESSELS

CROSS REFERENCE TO RELATED APPLICATIONS

The present application claims priority to and the benefit of the U.S. Provisional Patent Application No. 62/023,296, filed Jul. 11, 2014, which is hereby incorporated by reference in its entirety.

TECHNICAL FIELD

The present disclosure relates generally to the treatment of vessels and, in particular, the treatment of blockages or other restrictions to the flow of fluid through a vessel. Aspects of the present disclosure are particularly suited for evaluation of biological vessels in some instances. For example, some particular embodiments of the present disclosure are specifically configured for the treatment of one or more stenoses of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance predominantly by reducing the microcirculation resistance associated with the systolic portion of the heart cycle to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

In previous applications, the present applicants have described (a) improved devices, systems, and methods for assessing the severity of a blockage in a vessel and, in particular, a stenosis in a blood vessel that do not require the administration of hyperemic agents, (b) improved devices, systems, and methods for providing visual depictions of vessel that allow assessment of the vessel and, in particular, any stenosis or lesion of the vessel, and (c) improved devices, systems, and methods that simulate one or more available treatment options for the vessel, among other innovations. However, there remains a need for improved devices, systems, and methods for performing treatment of the blockage(s) or lesion(s) of the vessel, including guiding placement of one or more treatment devices, based on an assessment of the vessel and/or simulated treatment options.

SUMMARY

Embodiments of the present disclosure are configured to assess the severity of a blockage in a vessel and, in particular, a stenosis in a blood vessel, provide visual depictions of vessel that allow assessment of the vessel and, in particular, any stenosis or lesion of the vessel, simulate one or more treatment options for the vessel, and perform treatment on any stenosis or lesion of the vessel, including guiding placement of one or more treatment devices.

In some embodiments, methods of treating a vessel of a patient are provided. The method includes obtaining pressure measurements from first and second instruments positioned within a vessel of a patient during a diagnostic procedure where the second instrument is moved longitudinally through the vessel from a first position to a second position and the first instrument remains stationary within the vessel; identifying a treatment option based on the obtained pressure measurements; and performing the identified treatment option, wherein a user display guides placement of one or more treatment devices associated with the identified treatment option.

In some implementations, the first position is distal of at least one stenosis of the vessel and the second position is proximal of the at least one stenosis of the vessel such that moving the second instrument longitudinally through the vessel comprises a pullback. In some instances, the image is an intravascular image, such as an intravascular ultrasound (IVUS) image or an optical coherence tomography (OCT) image. In some instances, the image is an extravascular image, such as a two dimensional angiographic image, a three dimensional angiographic image, or a computed tomography angiographic (CTA) image.

In some implementations, the step of identifying a treatment option based on the obtained pressure measurements includes outputting an image of the vessel on the user display, the output image including visualizations based on the obtained pressure measurements. In that regard, the visualizations can include an intensity map based on changes in a pressure ratio of the obtained pressure measurements from the first and second instruments. For example, a first visual characteristic of the intensity map is associated with pressure ratios above a threshold value and a second visual characteristic of the intensity map is associated with pressure ratios below the threshold value. In some embodiments, the visualizations include a graph of a pressure ratio of the obtained pressure measurements from the first and second instruments. The graph is scaled, rotated, and mirror imaged, as necessary, to align the proximal and distal portions of the graph with the corresponding proximal and distal portions of the vessel as depicted in the image in some instances. In some embodiments, the visualizations include numerical values of a pressure ratio of the obtained pressure measurements from the first and second instruments. In some implementations, the visualizations include markings representative of a pressure ratio of the obtained pressure measurements from the first and second instruments. In that regard, the number of markings is representative of a relative change in the pressure ratio in some instances.

The step of identifying a treatment option can also include modifying the image of the vessel to simulate one or more treatment options. In that regard, modifying the image of the vessel to simulate one or more treatment options can include modifying the image of the vessel to simulate a first treatment option, modifying the image of the vessel to simulate a second treatment option, and evaluating the modified images of the vessel to select either the first treatment option or the second treatment option as the identified treatment option. In some instances, the treatment options include angioplasty, deploying one or more stents, applying a pharmaceutical agent, and combinations thereof.

In some instances, the placement of one or more treatment devices associated with the identified treatment option is guided by the user display showing a current location of the one or more treatment devices within the vessel along with a desired location of the one or more treatment devices within the vessel based on the identified treatment option. Further, in some implementations the placement of one or more treatment devices associated with the identified treatment option is guided by the user display showing a current location of the one or more treatment devices within the vessel along with a corresponding estimated treatment value associated with deploying the one or more treatment devices at the current location. In that regard, the estimated treatment value can be a visual representation of the expected effectiveness of deploying the one or more treatment devices at the current location relative to the originally obtained pressure measurements. For example, in some instances an expected pressure ratio value is displayed, which may be compared to the original pressure ratio value and/or a threshold value. Alternatively, the estimated treatment value can be a color indicating the expected effectiveness. Further, the display can include multiple estimated treatment values along the length of the vessel based. Accordingly, where multiple treatment devices are to be deployed, the various estimated treatment values can be utilized to guide placement of the different devices/treatments relative to one another and/or the vessel for optimal overall treatment effectiveness. Such an approach can be particularly beneficial in the context of diffuse lesions.

Systems for performing such methods are also provided.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 14*a* shows a treatment device at a first position within the vessel, FIG. 14*b* shows the treatment device at a second position within the vessel, and FIG. 14*c* shows the treatment device at a third position within the vessel.

FIG. 15*a* shows a treatment device at a first position within the vessel, FIG. 15*b* shows the treatment device at a second position within the vessel.

FIGS. 16*a*-16*c* illustrate visual depictions of a profile of the vessel that simulate deployment of the treatment device at the first, second, and third locations depicted in FIGS.

Figure 15A:
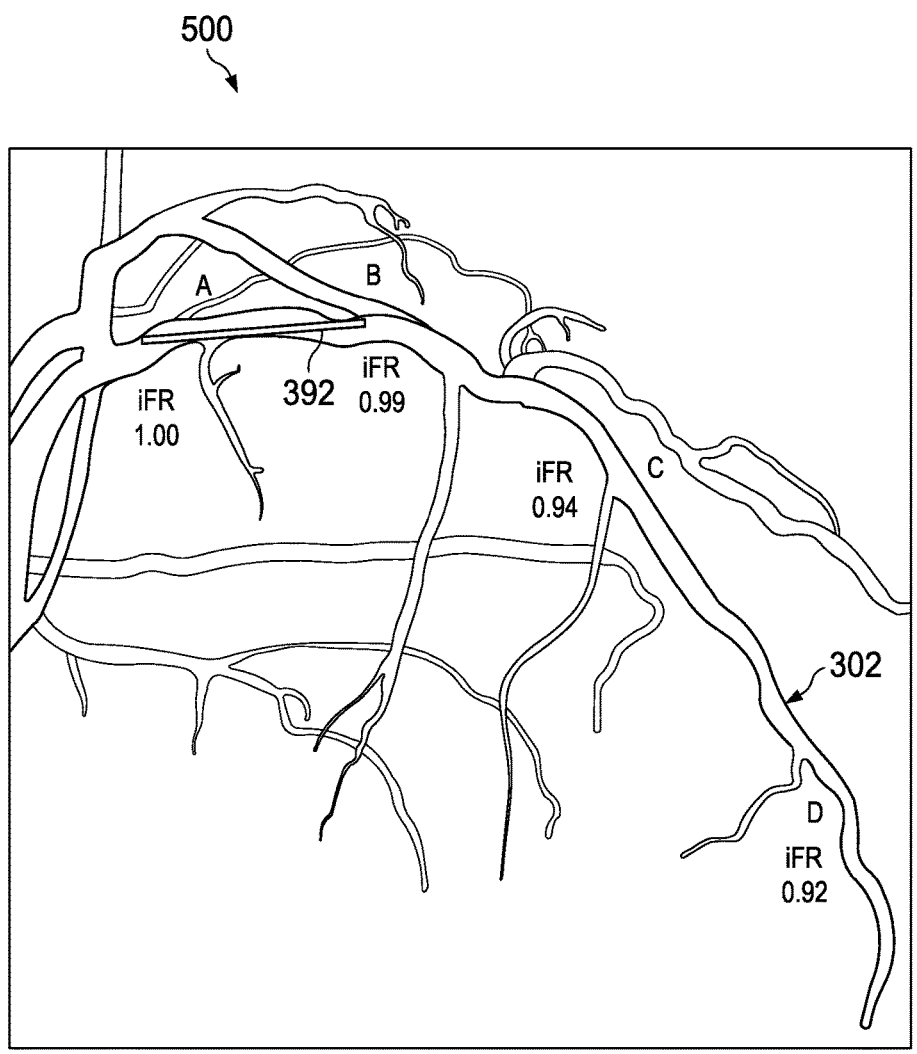
FIGS. 15*a*-15*c* illustrate annotated versions of an angiographic image to guide placement of a treatment device according to another embodiment of the present disclosure. In particular.
Figure 15B:
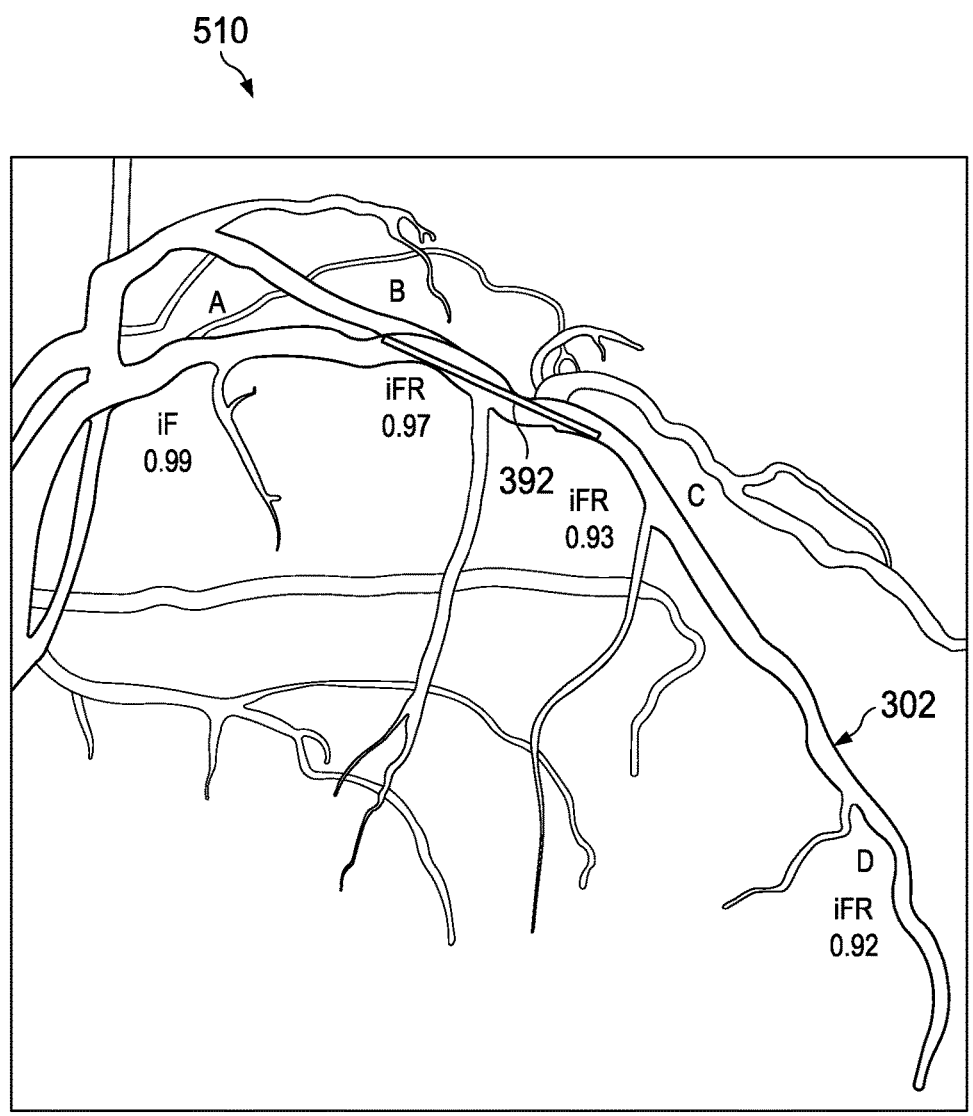

15a-15c. In particular, FIG. 16a provides visual depictions of a profile of the vessel with the treatment device at the first position within the vessel shown by FIG. 15a, FIG. 16b provides visual depictions of a profile of the vessel with the treatment device at the second position within the vessel shown by FIG. 15b, and FIG. 16c provides visual depictions of a profile of the vessel with the treatment device at the third position within the vessel shown by FIG. 15c.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
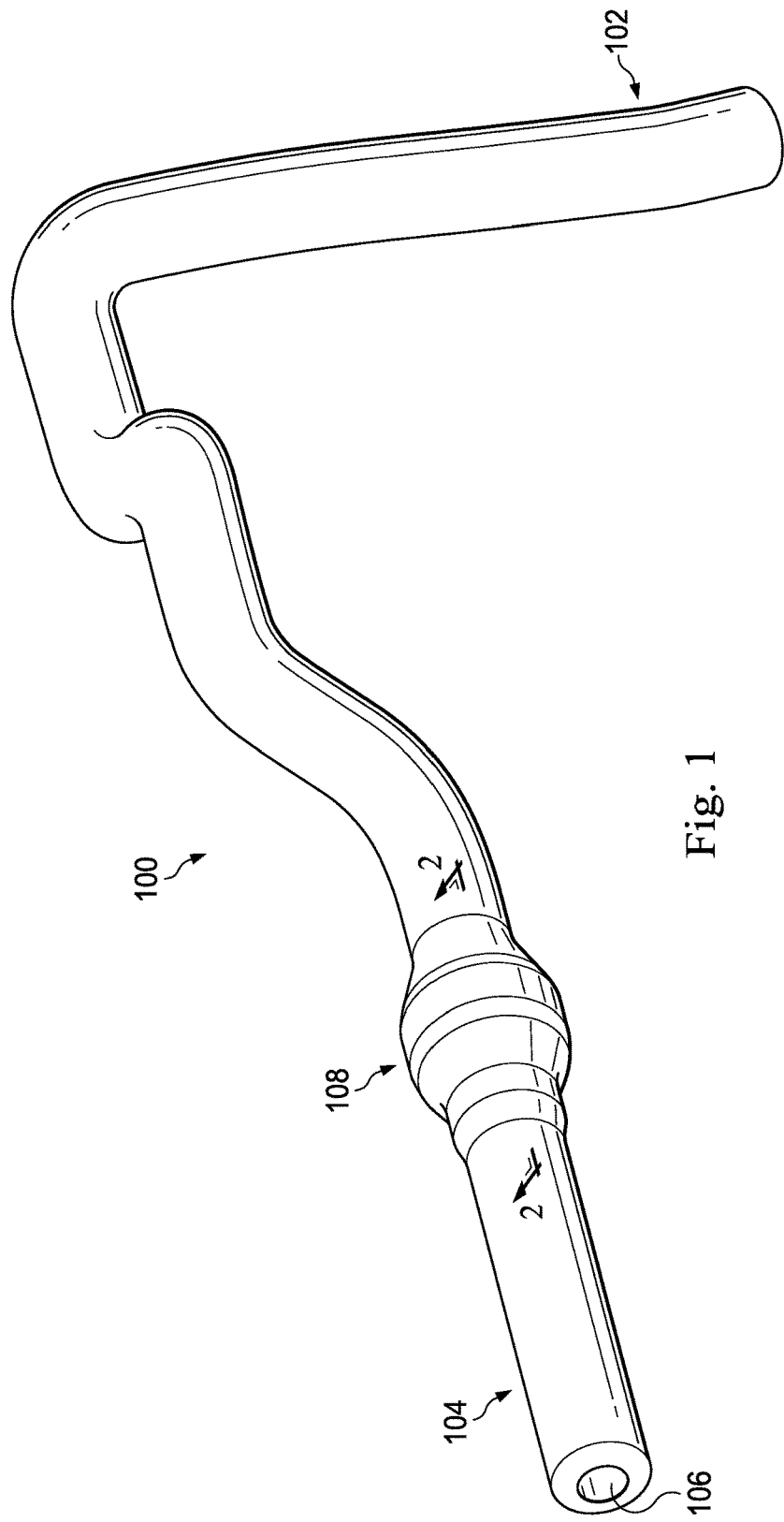
FIG. 1 is a diagrammatic perspective view of a vessel having a stenosis according to an embodiment of the present disclosure.
Figure 2:
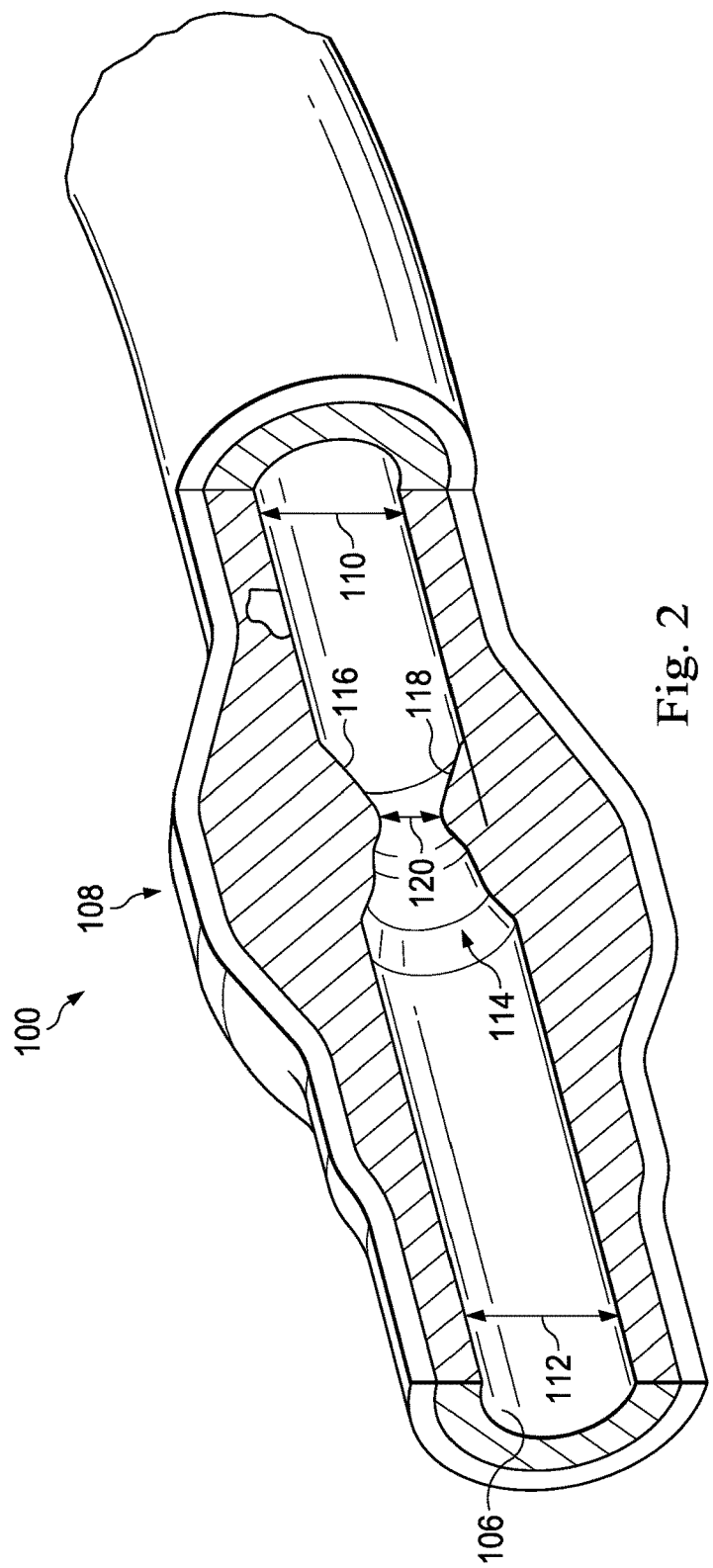
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should not be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
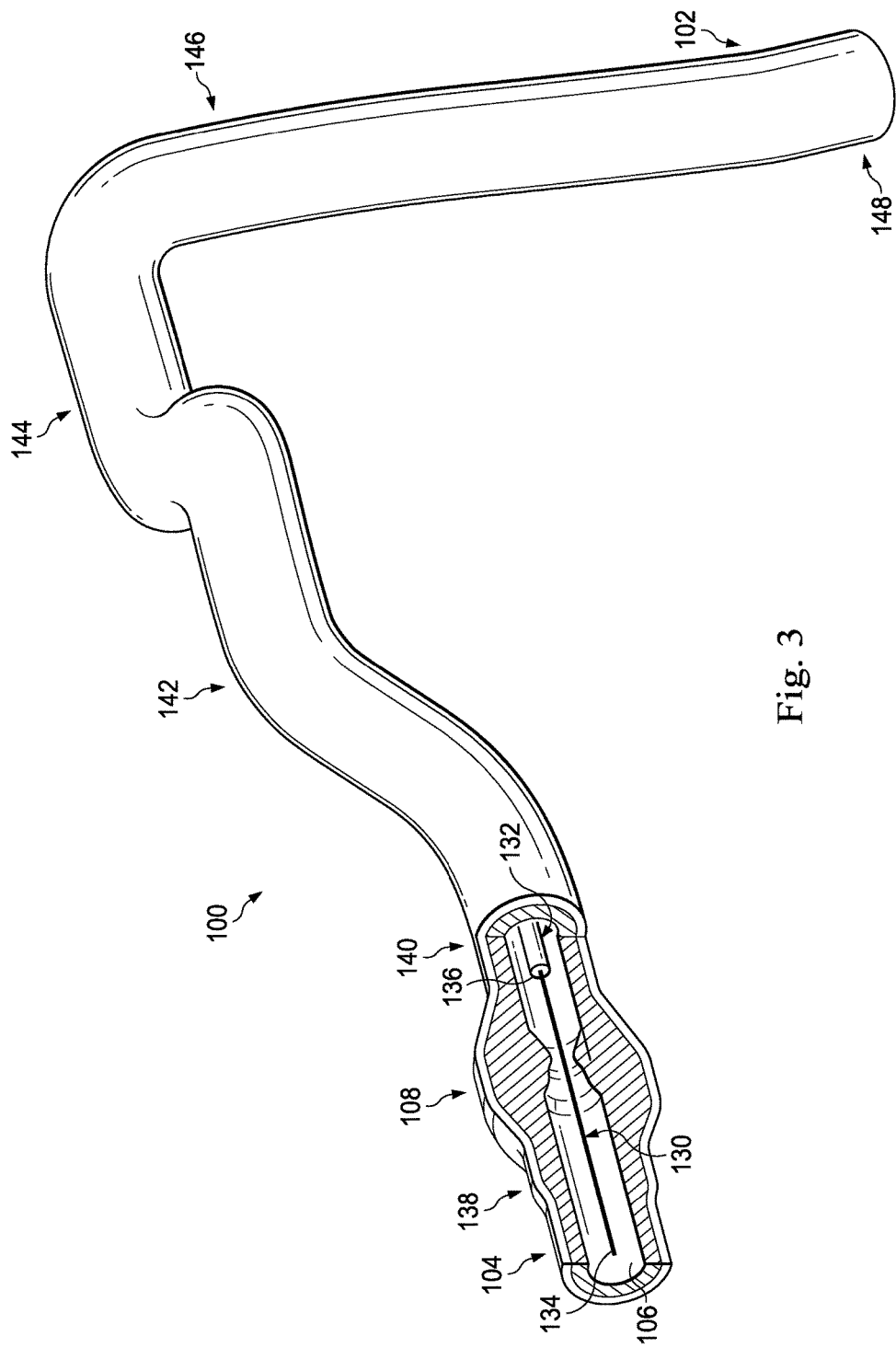
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In some embodiments, the single instrument incorporates aspects of the functionalities (e.g., data acquisition) of both instruments 130 and 132.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire™ Certus guide wire and the PressureWire™ Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of 0.018" or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Currently available catheter products suitable for use with one or more of Siemens AXIOM Sensis, Mennen Horizon XVu, and Philips Xper IM Physiomonitoring 5 and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

In some embodiments, at least one of the instruments 130 and 132 is configured to monitor pressure within the vessel 100 while being moved through the lumen 106. In some instances, instrument 130 is configured to be moved through the lumen 106 and across the stenosis 108. In that regard, the instrument 130 is positioned distal of the stenosis 108 and moved proximally (i.e., pulled back) across the stenosis to a position proximal of the stenosis in some instances. In other instances, the instrument 130 is positioned proximal of the stenosis 108 and moved distally across the stenosis to a position distal of the stenosis. Movement of the instrument 130, either proximally or distally, is controlled manually by medical personnel (e.g., hand of a surgeon) in some embodiments. In other embodiments, movement of the instrument 130, either proximally or distally, is controlled automatically by a movement control device (e.g., a pullback device, such as the Trak Back® II Device available from Volcano Corporation). In that regard, the movement control device controls the movement of the instrument 130 at a selectable and known speed (e.g., 2.0 mm/s, 1.0 mm/s, 0.5 mm/s, 0.2 mm/s, etc.) in some instances. Movement of the instrument 130 through the vessel is continuous for each pullback or push through, in some instances. In other instances, the instrument 130 is moved step-wise through the vessel (i.e., repeatedly moved a fixed amount of distance and/or a fixed amount of time). Some aspects of the visual depictions discussed below are particularly suited for embodiments where at least one of the instruments 130 and 132 is moved through the lumen 106. Further, in some particular instances, aspects of the visual depictions discussed below are particularly suited for embodiments where a single instrument is moved through the lumen 106, with or without the presence of a second instrument.

In some instances, use of a single instrument has a benefit in that it avoids issues associated with variations in pressure measurements of one instrument relative to another over time, which is commonly referred to as drift. In that regard, a major source of drift in traditional Fractional Flow Reserve (FFR) measurements is divergence in the pressure reading of a guidewire relative to the pressure reading of a guide catheter. In that regard, because FFR is calculated as the ratio of the pressure measurement obtained by the guidewire to the pressure measurement obtained by the catheter, this divergence has an impact on the resulting FFR value. In contrast, where a single instrument is utilized to obtain pressure measurements as it is moved through the vessel, drift is negligible or non-existent. For example, in some instances, the single instrument is utilized to obtain relative changes in pressures as it is moved through the vessel such that the time period between pressure measurements is short enough to prevent any impact from any changes in pressure sensitivity of the instrument (e.g., less than 500 ms, less than 100 ms, less than 50 ms, less than 10 ms, less than 5 ms, less than 1 ms, or otherwise).

Figure 4:
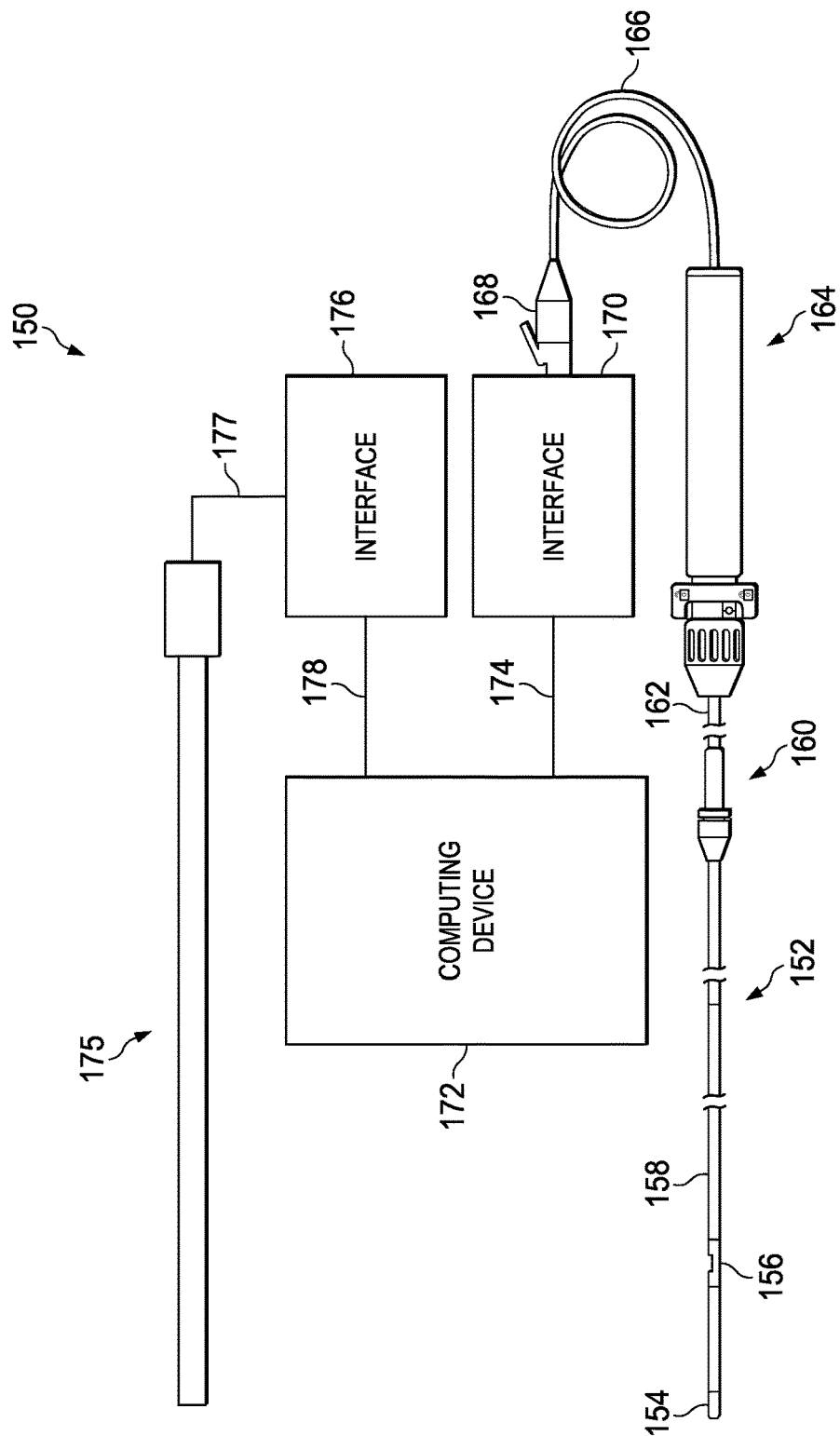
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above. Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Figure 5:
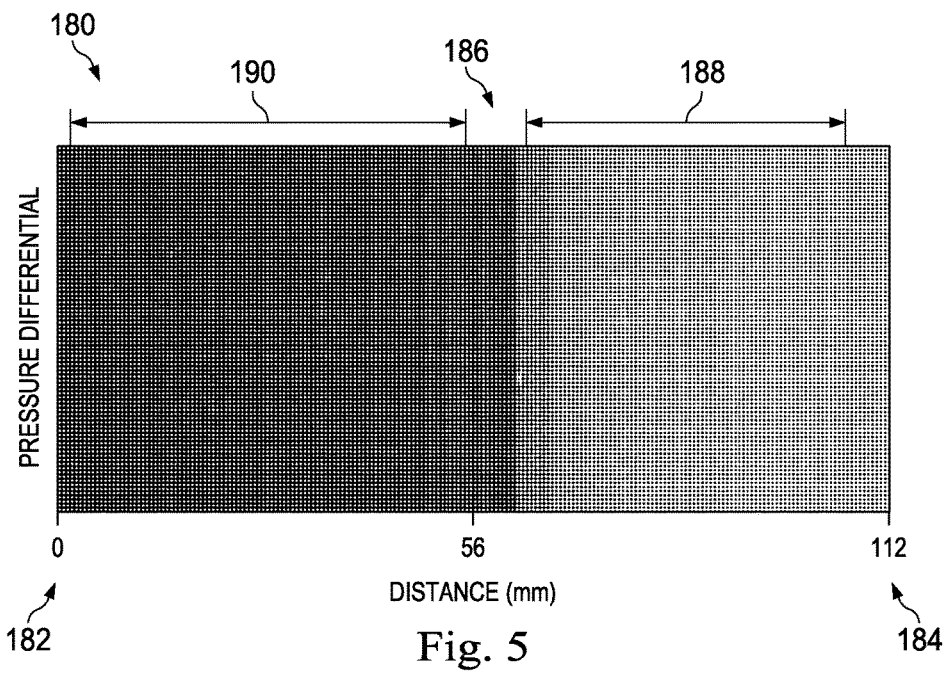
FIG. 5 is a visual depiction of a vessel profile based on pressure measurements according to an embodiment of the present disclosure.

Referring now to FIGS. 5-8, shown therein are various visual depictions of a vessel profile based on pressure measurements according to embodiments of the present disclosure. Referring more specifically to FIG. 5, shown therein is a visual representation 180 of a vessel. In that regard, visual representation 180 illustrates approximately a 112 mm segment of the vessel between points 182 and 184. In that regard, point 182 is representative of a starting position of an instrument within the vessel while point 184 is representative of an ending position of the instrument within the vessel after movement of the instrument longitudinally along the lumen of the vessel. Accordingly, in the instance of a pullback of the instrument, point 182 is distal of point 184 within the vessel. On the other hand, in the instance where the instrument pushed through the vessel, point 182 is proximal of the point 184. Regardless of the direction of movement of the instrument, the instrument will cross one or more lesions and/or stenosis of the vessel between the point 182 and the point 184. In that regard, each of the visual depictions of FIGS. 5-8 is configured to identify the one or more lesions and/or stenosis based on pressure measurements obtained from the instrument as the instrument is moved through the vessel.

Referring again to FIG. 5, visual representation 180 is a heat map that illustrates changes in pressure measurements obtained as the instrument is moved through the vessel. In that regard, in some instances the pressure measurements shown in the heat map are representative of a pressure differential between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer the fixed position of the distal pressure measurement). For clarity in understanding the concepts of the present disclosure, this arrangement will be utilized to describe many of the embodiments of the present disclosure. However, it is understood that the concepts are equally applicable to other arrangements. For example, in some instances, the instrument is pushed through the vessel from a first position distal of the proximal pressure measurement location to a second position further distal (i.e., further away from the fixed position of the proximal pressure measurement). In other instances, a distal pressure measurement is obtained at a fixed location within the vessel and the instrument is pulled back through the vessel from a first position proximal of the fixed location of the distal pressure measurement to a second position more proximal than the first position (i.e., further away from the fixed position of the distal pressure measurement). In still other instances, a distal pressure measurement is obtained at a fixed location within the vessel and the instrument is pushed through the vessel from a first position proximal of the fixed location of the distal pressure measurement to a second position less proximal than the first position (i.e., closer the fixed position of the distal pressure measurement).

The pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In some implementations, the difference in pressure is calculated as Pd/Pa, Pd−Pa, or other suitable calculation for each heartbeat cycle. In some instances, the difference in pressure may be referred to as the pressure gradient. In that regard, a mean, median, mode, and/or other suitable value (e.g., filtering to remove outliers, then using mean, median, and/or mode, etc.) is calculated and utilized for each of Pa and Pd for each heartbeat cycle. In that regard, in some instances the mean, median, mode, and/or other suitable value used to represent Pa and/or Pd for each heartbeat cycle is calculated using the pressure data within the diagnostic window(s) for each heartbeat cycle. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances. In that regard, in some embodiments a diagnostic window is selected using one or more of the techniques described in U.S. patent application Ser. No. 13/460,296, filed Apr. 30, 2012 published as U.S. Patent Application Publication No. 2013/0046190 on Feb. 21, 2013 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In some embodiments, the determination of the diagnostic window and/or the calculation of the pressure differential are performed in approximately real time or live to identify the section 212 and calculate the pressure differential. In that regard, calculating the pressure differential in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure differential calculation is performed 10 or more seconds after data acquisition. For example, in some embodiments, the data utilized to identify the diagnostic window and/or calculate the pressure differential are stored for later analysis.

By comparing the calculated pressure differential to a threshold or predetermined value, a physician or other treating medical personnel can determine what, if any, treatment should be administered. In that regard, in some instances, a calculated pressure differential above a threshold value (e.g., 0.80 on a scale of 0.00 to 1.00) is indicative of a first treatment mode (e.g., no treatment, drug therapy, etc.), while a calculated pressure differential below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In that regard, the coloring and/or other visually distinguishing aspect of the pressure differential measurements depicted in visual representation 180 of FIG. 5 are configured based on the threshold value. For example, a first color (e.g., green, white, or otherwise) is utilized to represent values well above the threshold value (e.g., where the threshold value is 0.80 on a scale of 0.00 to 1.00, values above 0.90), a second color (e.g., yellow, gray, or otherwise) is utilized to represent values near but above the threshold value (e.g., where the threshold value is 0.80 on a scale of 0.00 to 1.00, values between 0.81 and 0.90), and a third color (e.g., red, black, or otherwise) is utilized to represent values equal to or below the threshold value (e.g., where the threshold value is 0.80 on a scale of 0.00 to 1.00, values of 0.80 and below). It is appreciated that any number of color combinations, scalings, categories, and/or other characteristics can be utilized to visually represent the relative value of the pressure differential to the threshold value. However, for the sake of brevity Applicants will not explicitly describe the numerous variations herein.

As shown in FIG. 5, the heat map of visual representation 180 utilizes a gray scale where lighter or whiter colors are representative of values above the threshold value, while darker or blacker colors are representative of values near or below the threshold value. In that regard, the heat map of visual representation 180 is based on a cumulative or total pressure differential, where the gray scale color selected for a particular point is determined based on the pressure differential between the instrument at that point being moved through the vessel and the stationary or fixed instrument. As shown, in the illustrated embodiment a transition point or area 186 of the vessel is positioned between a portion 188 of the vessel having pressure differential values above the threshold value and a portion 190 of the vessel having pressure differential values below the threshold value. In that regard, the transition point or area 186 is representative of a boundary of a lesion or stenosis of the vessel that results in an increased pressure differential, which is illustrated by the change in color of the visual representation 180. As a result, the visual representation 180 can be utilized to both identify the location of the lesion or stenosis within the vessel and assess the severity of the lesion or stenosis.

Figure 6:
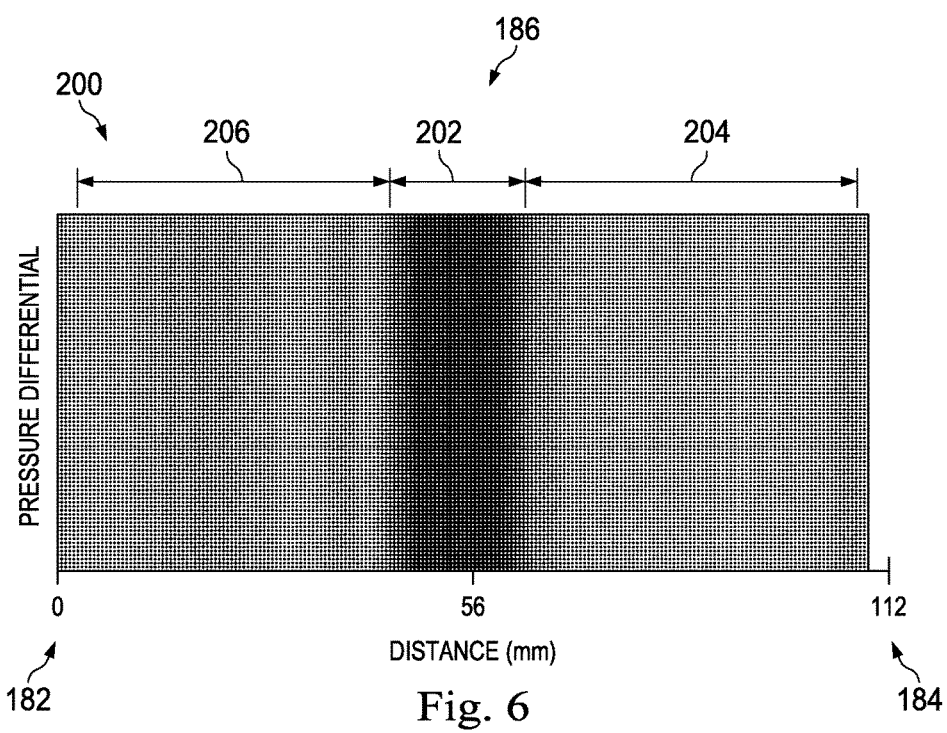
FIG. 6 is a visual depiction of a vessel profile based on pressure measurements similar to that of FIG. 5, but illustrating an alternative embodiment of the present disclosure.

Referring now to FIG. 6, shown therein is a visual representation 200 of a vessel profile based on the same pressure measurements as the visual representation 180 of FIG. 5. In that regard, the heat map of visual representation 200 also utilizes a gray scale where lighter or whiter colors are representative of values above a threshold value, while darker or blacker colors are representative of values near or below the threshold value. While the heat map of visual representation 180 was based on a cumulative or total pressure differential, the heat map of visual representation 200 is based on a localized pressure differential, where the gray scale color selected for a particular point is determined based on differences between the pressure differential of that point with one or more of the surrounding points. In that regard, the localized pressure differential is calculated as the difference between the immediately preceding point in some instances. For example, the localized pressure differential for point $P_n$ is equal to the cumulative or total pressure differential for point $P_n$ minus the total or cumulative pressure differential for point $P_{n-1}$. In other instances, the localized pressure differential is calculated as the difference between that point and a point a fixed amount of time (e.g., 10 ms, 5 ms, 2 ms, 1 ms, or otherwise) or distance (e.g., 10 mm, 5 mm, 2 mm, 1 mm, or otherwise) away from that point. By utilizing a localized pressure differential the location of significant changes in pressure differential values, which are often associated with the presence of a lesion or stenosis, can be identified.

For example, as shown in the illustrated embodiment of FIG. 6, a transition area 202 of the vessel having localized pressure differential values below the threshold is positioned between portions 204 and 206 of the vessel having pressure differential values above the threshold value. In that regard, the transition point or area 202 is representative of a lesion or stenosis of the vessel that results in a significant change in pressure differential, which is illustrated by the change in color of the visual representation 200. As a result, the visual representation 200 can be utilized to both identify the location of the lesion or stenosis within the vessel and assess the severity of the lesion or stenosis.

Figure 7:
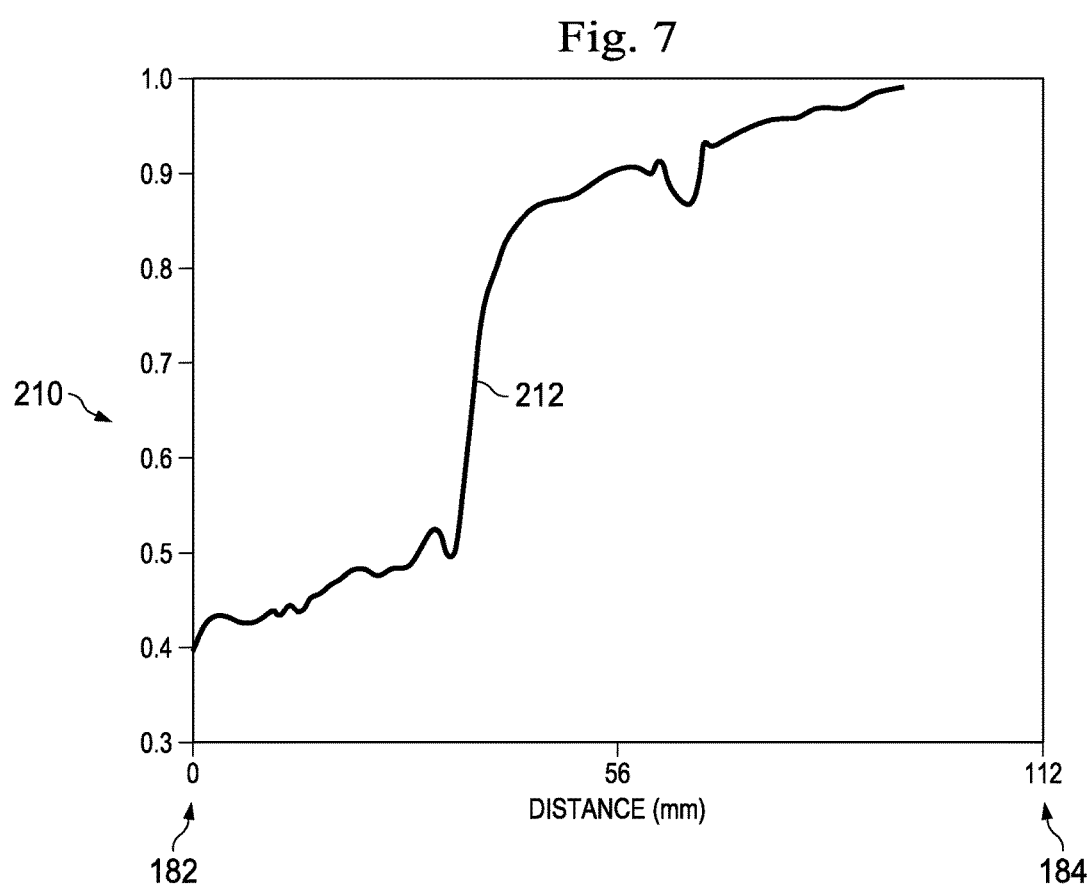
FIG. 7 is a visual depiction of a vessel profile based on pressure measurements according to another embodiment of the present disclosure.

Referring now to FIG. 7, shown therein is a visual representation 210 of a vessel profile based on the same pressure measurements as the visual representations 180 and 200 of FIGS. 5 and 6, respectively. In that regard, FIG. 7 illustrates a plot 212 of the cumulative or total pressure differential between the instrument being moved through the vessel and an instrument at a stationary or fixed position within the vessel. By analyzing the shape of the plot 212 and, in particular, such characteristics as the pressure differential value relative to the threshold value, changes in the slope of the plot, and/or combinations thereof, the visual representation 210 can be utilized to both identify the location of the lesion or stenosis within the vessel and assess the severity of the lesion or stenosis.

Figure 8:
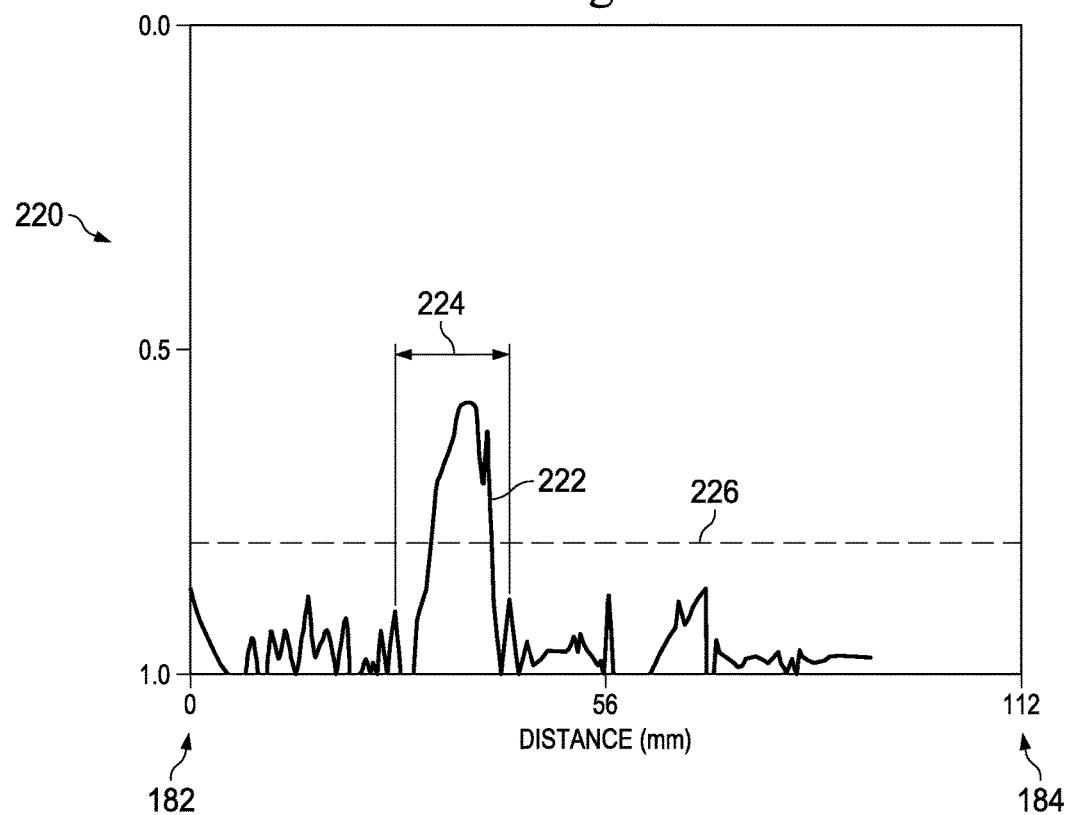
FIG. 8 is a visual depiction of a vessel profile based on pressure measurements according to another embodiment of the present disclosure.

Referring now to FIG. 8, shown therein is a visual representation 220 of a vessel profile based on the same pressure measurements as the visual representations 180, 200, and 210 of FIGS. 5, 6, and 7, respectively. In that regard, FIG. 8 illustrates a plot 222 that is based on differences between the pressure differential of a point with one or more of the surrounding points. In that regard, the values utilized for plot 222 are calculated as the difference between adjacent points in some instances. For example, the value for point $P_n$ is equal to the cumulative or total pressure differential for point $P_n$ minus the total or cumulative pressure differential for point $P_{n-1}$, in some instances. In other instances, the value utilized a particular point of plot 222 is calculated as the difference between the pressure differential for that point and another point a fixed amount of time (e.g., 10 ms, 5 ms, 2 ms, 1 ms, or otherwise) or distance (e.g., 10 mm, 5 mm, 2 mm, 1 mm, or otherwise) away from that point. In the illustrated embodiment, plot 222 is based upon the differences in pressure differential between points 2 mm apart from one another. Utilizing these relative and localized calculations of pressure differential, the location of significant changes in pressure differential values that are associated with the presence of a lesion or stenosis can be identified.

The plot 222 can be utilized to both identify the location of lesions or stenosis within the vessel as well as assess the severity of the identified lesions or stenosis. In the illustrated embodiment of FIG. 8, a region 224 of the plot 222 does not meet the threshold value indicated by line 226. In that regard, it should be noted that in FIG. 8, the y-axis values of the visual representation 220 go from 1.0 at the origin to 0.0 at the top of the illustrated y-axis. Accordingly, region 224 represents a lesion or stenosis of the vessel that is adversely impacting fluid flow to a degree that requires treatment. Analysis of the plot 222 provides information about the vessel and/or its lesions or stenosis. For example, the plot 222 provides an indication of the length of the lesion or stenosis associated with region 224. In that regard, the length of the lesion or stenosis is indicated by the length of the vessel segment having values less than the threshold value 226. In the illustrated embodiment, the length of the vessel segment having values less than the threshold value 226 is approximately 17 mm. The length of the lesion or stenosis as indicated by the plot 222 is based entirely on physiologic measurements that are independent of lesion composition.

Further, the plot 222 provides an indication of the overall occlusive value of the vessel. In that regard, the total vessel occlusive value is determined by cumulative area under the plot 222 in some instance. In the illustrated embodiment, the total vessel occlusive value or area under the plot 222 is approximately 1.38. Similarly, the plot 222 also provides an indication of the occlusive value attributable to individual lesions or stenosis of the vessel. In that regard, the occlusive value attributable to a particular lesion or stenosis can similarly be calculated by determining the area under the plot 222 for a length of the vessel associated with the lesion or stenosis. For example, in the illustrated embodiment the lesion or stenosis associated with region 224 has an occlusive value or area under the plot 222 of approximately 0.67. Based on the total vessel occlusive value and the occlusive value attributable to a particular lesion or stenosis, a percentage of the total vessel occlusive value attributable to that particular lesion or stenosis can be calculated. In that regard, the ratio of the occlusive value attributable to the particular lesion or stenosis to the total occlusive value of the vessel provides the percentage of vessel occlusion attributable to that lesion or stenosis. The information regarding characteristics of the lesion or stenosis and/or the vessel as indicated by the plot 222 can be compared with or considered in addition to other representations of the lesion or stenosis and/or the vessel (e.g., IVUS (including virtual histology), OCT, ICE, Thermal, Infrared, flow, Doppler flow, and/or other vessel data-gathering modalities) to provide a more complete and/or accurate understanding of the vessel characteristics. For example, in some instances the information regarding characteristics of the lesion or stenosis and/or the vessel as indicated by the plot 222 are utilized to confirm information calculated or determined using one or more other vessel data-gathering modalities.

While the visual representations 180, 200, 210, and 220 of FIGS. 5, 6, 7, and 8 have been described separately. It is understood that a system may display any combination of these visual representations in series, simultaneously, and/or combinations thereof. In some instances, a system provides the user the ability to select which individual visual representation and/or combination of visual representations will be displayed. Further, generally speaking, the representation of the data in the visual representations can be utilized to identify gradients/changes in the pressure ratio and/or the underlying pressure measurements that can be indicative of a significant lesion in the vessel. In that regard, the visual representation of the data can include the pressure measurement(s); a ratio of the pressure measurements; a difference in the pressure measurements; a gradient of the pressure measurement(s), the ratio of the pressure measurements, and/or the difference in the pressure measurements; first or second derivatives of the pressure measurement(s), the ratio of the pressure measurements, and/or the difference in the pressure measurements; and/or combinations thereof.

Figure 9:
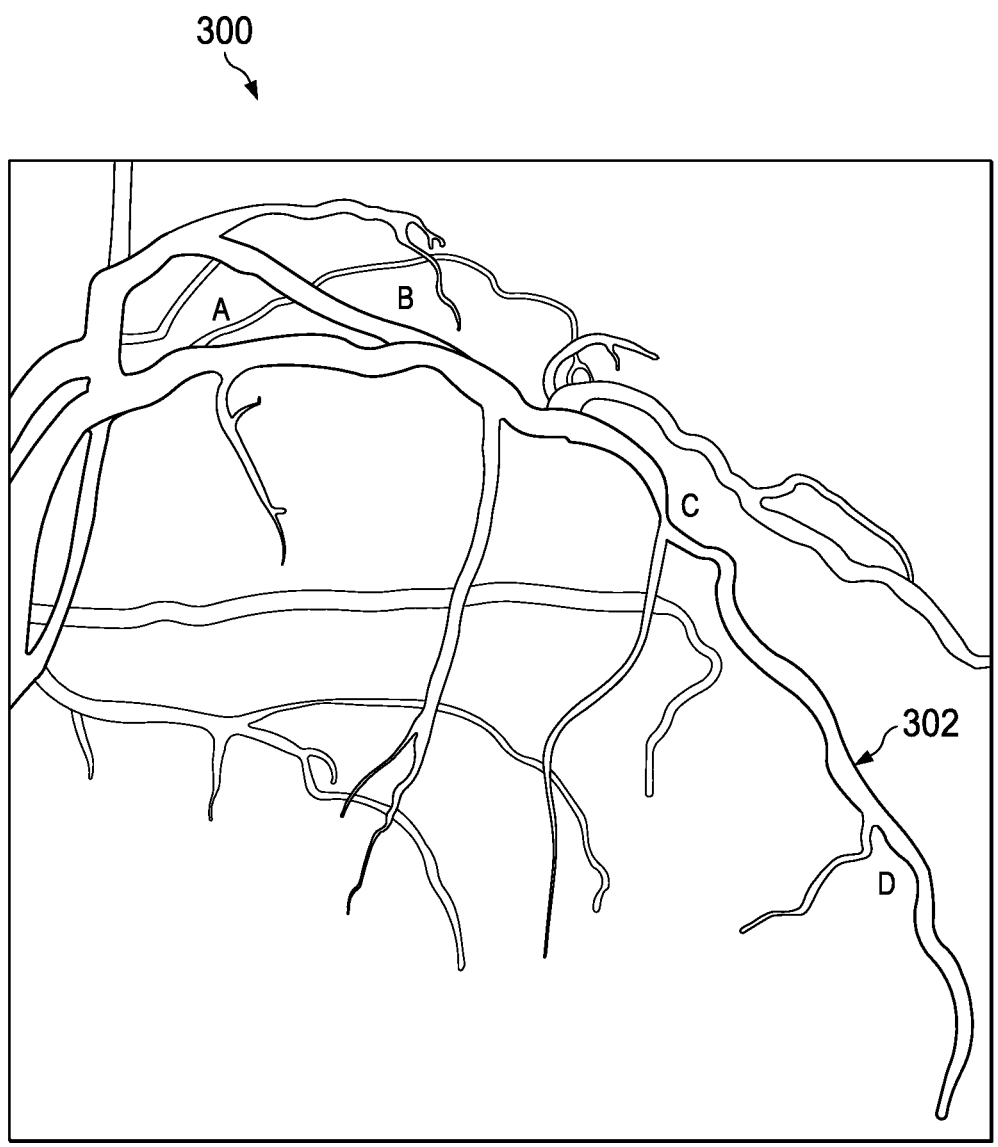
FIG. 9 is an angiographic image of a vessel according to an embodiment of the present disclosure.
Figure 10:
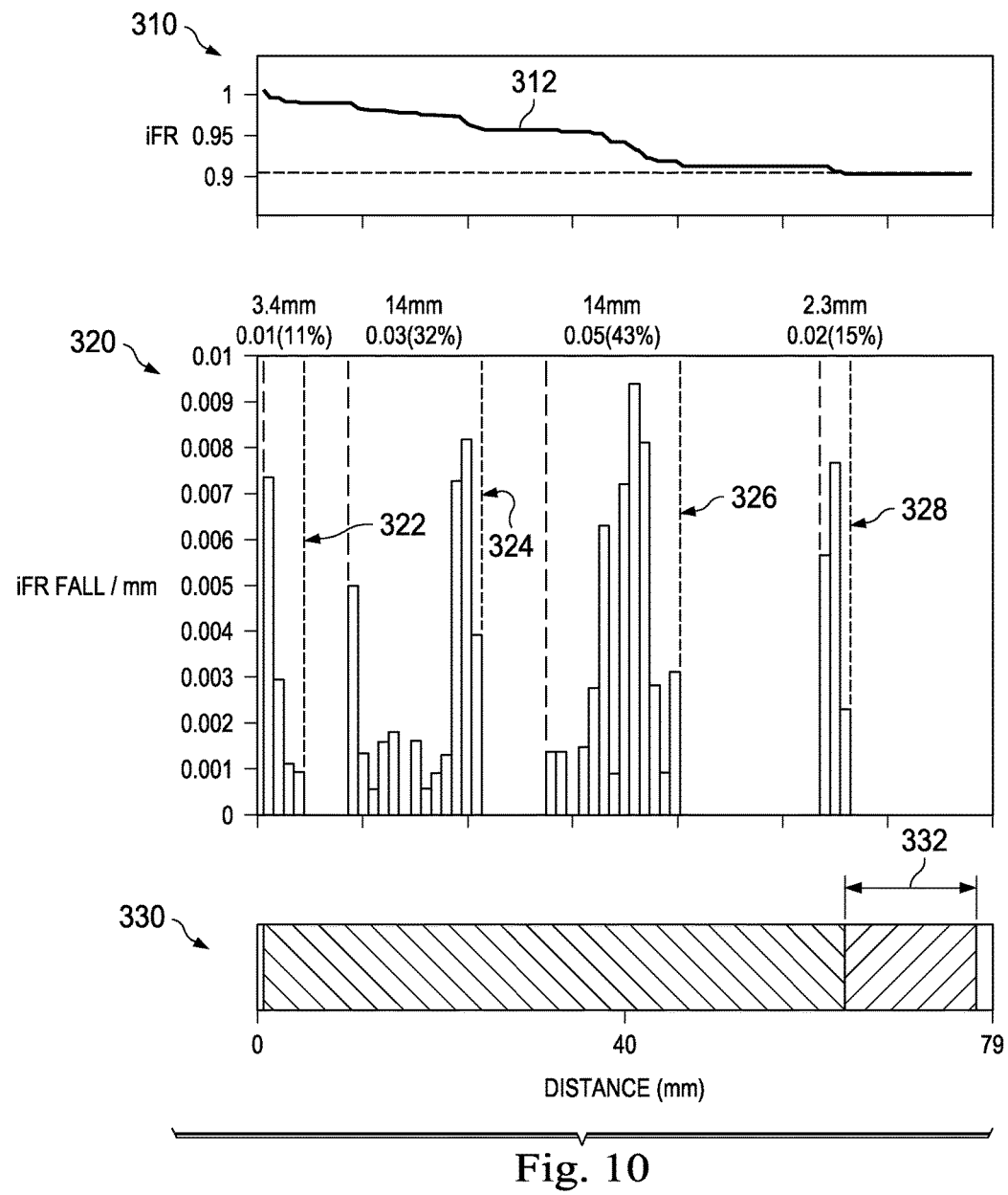
FIG. 10 provides visual depictions of a profile of the vessel of FIG. 9 based on pressure measurements according to an embodiment of the present disclosure.

Referring now to FIGS. 9-13, shown therein are aspects of evaluating a vessel according to embodiments of the present disclosure. In that regard, FIG. 9 provides an angiographic image 300 of a vessel 302 having a plurality of lesions or stenoses. In the illustrated embodiment, four lesions/stenoses are labeled as "A", "B", "C", and "D". Referring now to FIG. 10, shown therein is a graph 310 mapping a pressure ratio value calculated using a diagnostic window in accordance with the present disclosure, which may be referred to as "iFR" in the drawings, relative to a distance as a first instrument is moved through a vessel relative to a second instrument, including across at least one stenosis of the vessel. In that regard, the second instrument is maintained in a position proximal of the at least one stenosis while the first instrument is moved from a position distal of the at least one stenosis to a position proximal of the at least one stenosis and adjacent the second instrument or vice versa (i.e., the first instrument is moved from a position proximal of the at least one stenosis and adjacent the second instrument to a position distal of the at least one stenosis). In the illustrated embodiment of FIG. 10, the relative position of the first instrument as depicted in plot 312 transitions from proximal to distal as the plot 312 extends from left to right.

FIG. 10 also provides a bar graph 320 that depicts the change in pressure ratio values as depicted in graph 310 over distance. In that regard, the larger bars represent greater changes in pressure ratio value over that distance, which can be indicative of a sever lesion or stenosis. As shown, the bar graph 320 has been annotated to identify regions 322, 324, 326, and 328 that have notable changes in pressure ratio values. More specifically, the regions 322, 324, 326, and 328 correspond with lesions/stenoses A, B, C, and D of vessel 302, respectively.

Finally, FIG. 10 also provides an intensity map visual representation 330 (similar to visual representation 180 of FIG. 5) for the vessel 302 based on the pressure ratio values from graph 310. More specifically, the intensity map 330 identifies a region 332 where the pressure ratio is below the threshold value. In the illustrated embodiment, the threshold pressure ratio value is 0.90. Accordingly, the portions of the intensity map 330 left of region 332 are colored or otherwise visualized to indicate that the pressure ratio is above the threshold value, while the portions of the intensity map within region 332 are colored or otherwise visualized to indicate that the pressure ratio is below the threshold value. In the illustrated embodiment, a green color is utilized to represent values above the threshold value, while a red color is utilized to represent values near or below the threshold value.

Figure 11:
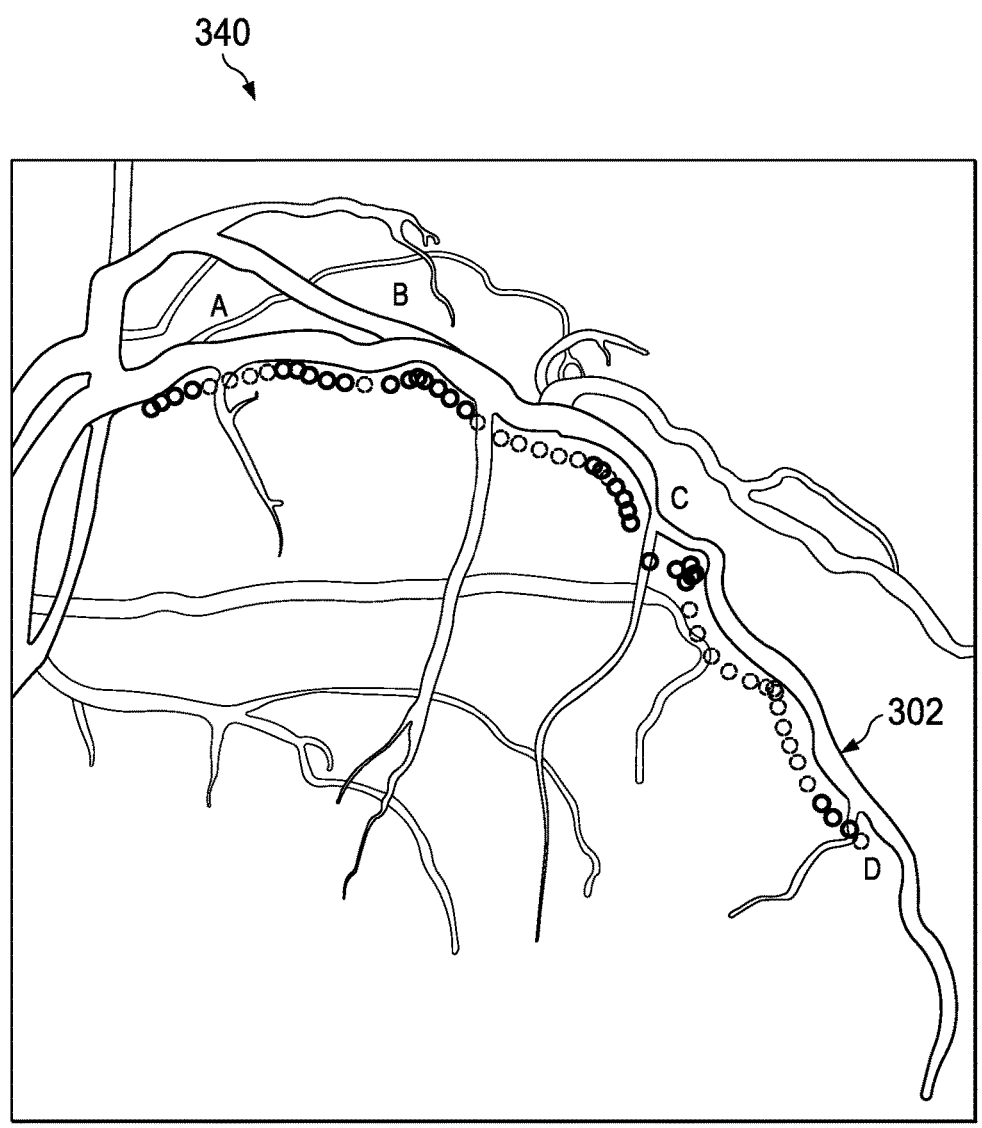
FIG. 11 is an annotated version of the angiographic image of FIG. 9 based on the profile information of FIG. 10 according to an embodiment of the present disclosure.

Referring now to FIG. 11, shown therein is an annotated angiographic image 340 of the vessel 302. In that regard, the angiographic image 300 of FIG. 9 has been annotated based on the pressure measurements obtained for vessel 302. More specifically, based on the changes in the pressure ratio along the length of the vessel (e.g., as depicted in the bar graph 320 of FIG. 10) corresponding visual indicators have been added to the angiographic image. In particular, in the illustrated embodiment colored circles have been added along the length of the vessel to provide a visual indication to the user of the amount of change in pressure ratio attributable to that portion of the vessel. In some implementations, the portions of the vessel having a change in pressure ratio less than a threshold value are colored or otherwise visualized to indicate that the change in pressure ratio is below the threshold value, while the portions of the vessel having a change in pressure ratio greater than the threshold value are colored or otherwise visualized to indicate that the change in pressure ratio is above the threshold value. In the illustrated embodiment, a green colored circle is utilized to represent values above the threshold value, while a red colored circle is utilized to represent values near or below the threshold value.

Further still, in some embodiments the color(s) or other feature(s) of the visual indicators are selected to reflect the type of tissue/plaque present at that location along the vessel. For example, in some instances the tissue/plaque of the vessel is characterized based on intravascular imaging (e.g., IVUS or spectroscopy) to identify the type(s) of tissue/plaque present. Then, based on the type(s) of tissue/plaque present, corresponding color(s), label(s), and/or other feature(s) of the visual indicators are utilized to provide an indication to the user of the type(s) of tissue/plaque present. In that regard, the type(s) of tissue/plaque present in the vessels can determine whether certain treatment options are suitable for not. In some instances, the tissue/plaque characterization is performed as described in one or more of U.S. Pat. No. 6,200,268, U.S. Pat. No. 6,381,350, U.S. Pat. No.

7,074,188, U.S. Pat. No. 7,175,597, U.S. Pat. No. 7,215,802, U.S. Pat. No. 7,359,554, and U.S. Pat. No. 7,463,759, each of which is hereby incorporated by reference in its entirety.

Figure 12:
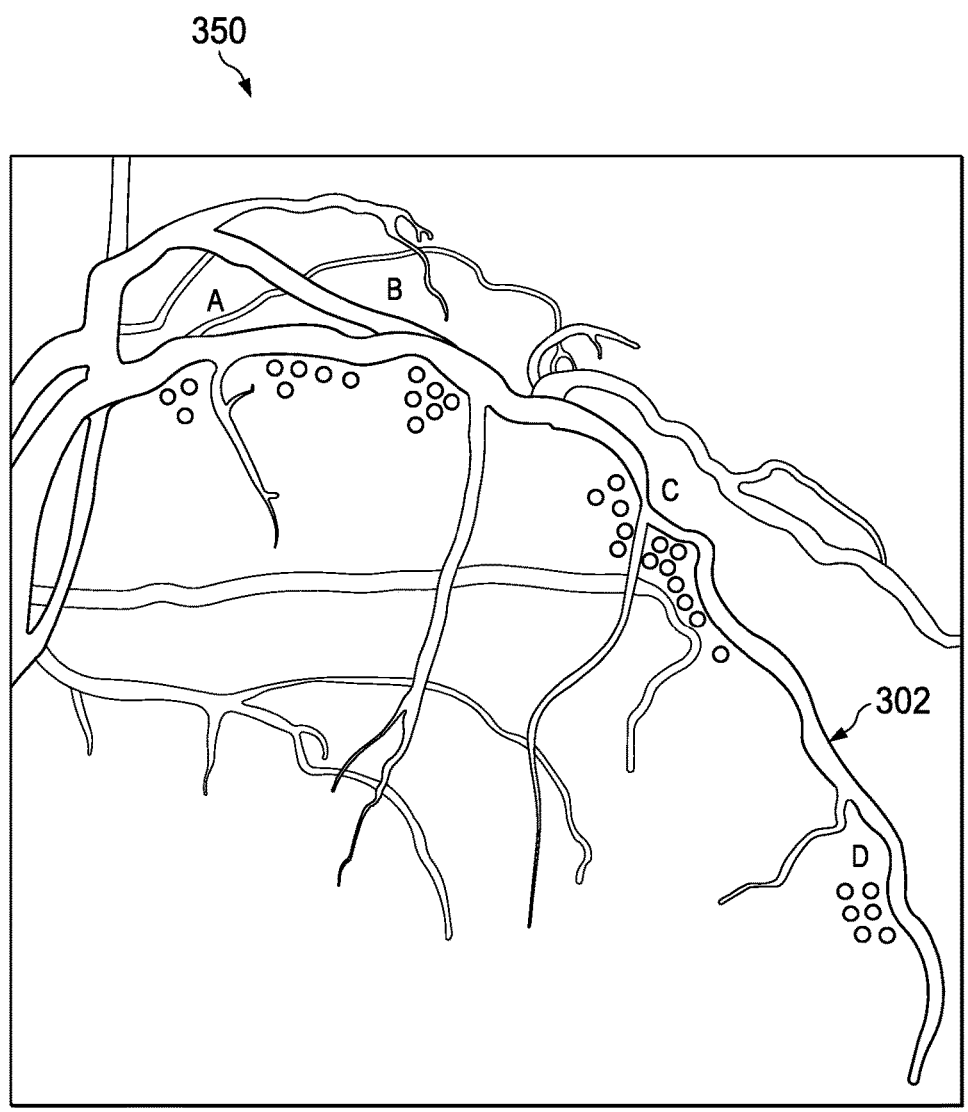
FIG. 12 is an annotated version of the angiographic image of FIG. 9 based on the profile information of FIG. 10 according to another embodiment of the present disclosure.

Referring now to FIG. 12, shown therein is an annotated angiographic image 350 of the vessel 302. In that regard, the angiographic image 300 of FIG. 9 has been annotated based on the pressure measurements obtained for vessel 302. More specifically, based on the changes in the pressure ratio along the length of the vessel (e.g., as depicted in the bar graph 320 of FIG. 10) corresponding visual indicators have been added to the angiographic image. In particular, in the illustrated embodiment dots have been added along the length of the vessel to provide a visual indication to the user of the amount of change in pressure ratio attributable to that portion of the vessel. More specifically, the greater the number of dots adjacent a portion of the vessel, the greater the change in pressure attributable to that portion of the vessel. In that regard, in some implementations the number of dots is directly correlated to values in bar graph 320 of FIG. 10.

It is understood that numerous other visualization techniques may be utilized to convey the information of the graphs 310, 320, and/or 330 of FIG. 10 in the context of an angiographic image or other image of the vessel (including both intravascular and extravascular imaging techniques, such as IVUS, OCT, ICE, CTA, etc.) to help the user evaluate the vessel. In that regard, while the examples of the present disclosure are provided with respect to angiographic images, it is understood that the concepts are equally applicable to other types of vessel imaging techniques, including intravascular and extravascular imaging. However, for the sake brevity the present disclosure will limit the examples to angiographic images.

In some instances an intensity map (such as described in the context of FIGS. 5, 6, and/or 10) is overlaid onto or adjacent to the vessel 302 as depicted in angiographic image such that the lesion specific contributions and/or cumulative effects of the lesions can be visualized in the context of the vessel itself. In that regard, it is understood that for any of the visualization techniques the pressure data can be related to the corresponding portions of the vessel 302 using co-registration techniques (such as those disclosed in U.S. Pat. No. 7,930,014, titled "VASCULAR IMAGE CO-REGISTRATION," which are hereby incorporated by reference in their entirety), based on the known pullback speed/distance, based on a known starting point, based on a known ending point, and/or combinations thereof. Further, in some embodiments the angiographic image is annotated with the numerical values associated with the pressure ratios and/or changes in pressure ratios. In some instances, a threshold value is set by the user or system (e.g., a default setting) such that values above or below the threshold, as the case may be, are identified. In that regard, the identified values can be presented to the user in chart form, added to the angiographic or other image of the vessel in the appropriate location, and/or combinations thereof. Further still, in some embodiments a graph similar to graph 410 and/or graph 420 is overlaid onto the angiographic or other image of the vessel. In that regard, the graph is scaled and oriented (i.e., positioned, rotated, and/or mirror imaged) to align with the general or average pathway of the vessel as depicted on the angiographic or other image of the vessel. In some implementations, diagnostic information and/or data is correlated to vessel images using techniques similar to those described in U.S. patent application Ser. No. 14/144,280 filed Dec. 30, 2013, published as U.S. Patent Application Publication No. 2014/0187920 on Jul. 3, 2014, titled "SPATIAL CORRELATION OF INTRAVASCULAR IMAGES AND PHYSIOLOGICAL FEATURES", which is hereby incorporated by reference in its entirety.

In some instances, a user is able to select what information should be included or excluded from the displayed image. In that regard, it should be noted that these visualization techniques related to conveying the pressure measurement data in the context of an angiographic or other image of the vessel can be utilized individually and in any combinations. For example, in some implementations a user is able to select what visualization mode(s) and/or portions thereof will be utilized and the system outputs the display accordingly. Further, in some implementations the user is able to manually annotate the displayed image to include notes and/or input one or more of the measured parameters.

Figure 13:
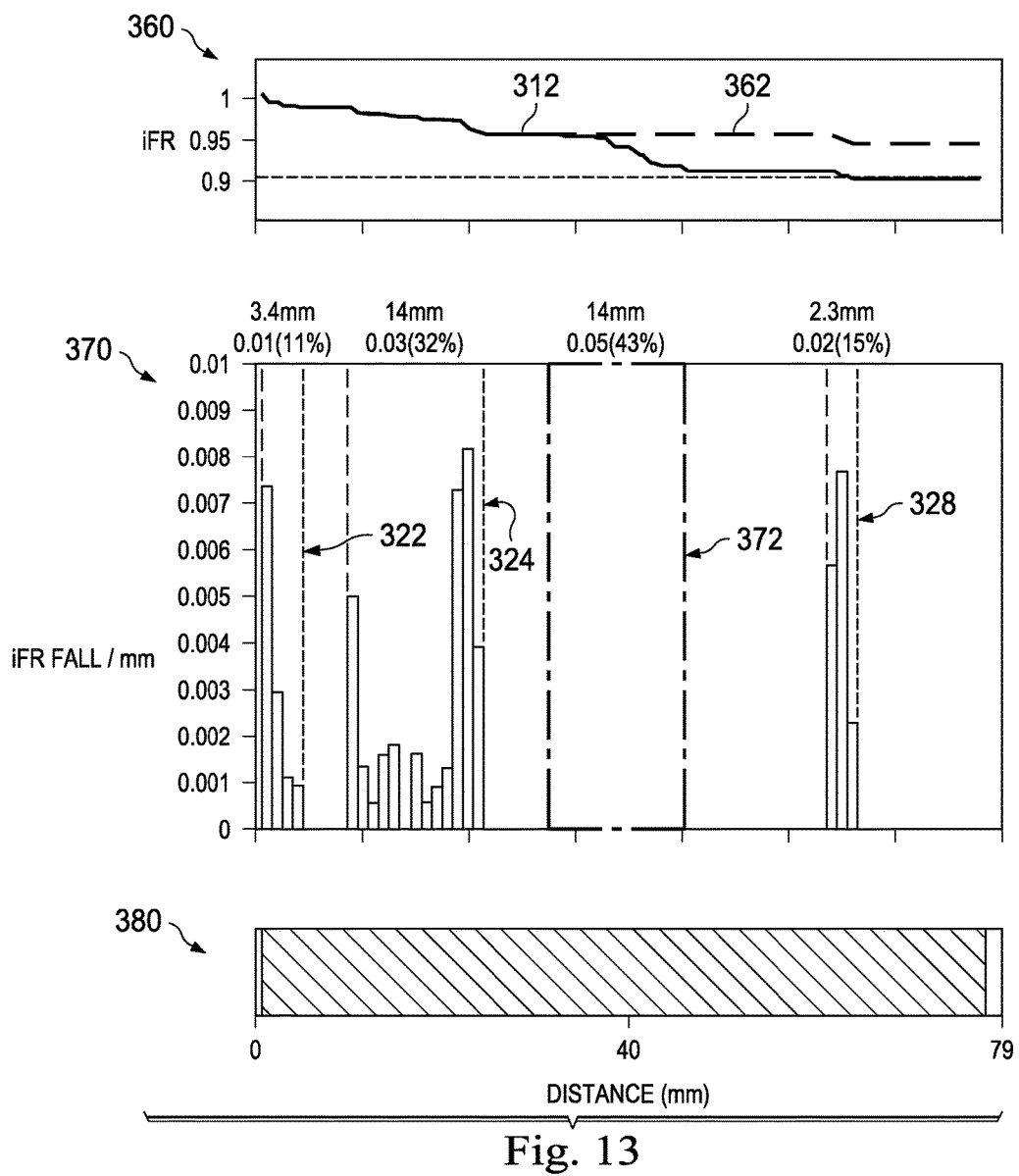
FIG. 13 provides visual depictions of a profile of the vessel of FIG. 9 similar those of FIG. 10, but simulating a treatment option according to an embodiment of the present disclosure.

Referring now FIG. 13, shown therein is a graph 360 that includes a plot 362 representative of simulated pressure ratio value calculations for a proposed treatment option for vessel 302 along with the plot 312 of the original pressure ratio value calculations. In that regard, the plot 362 is based upon removing the effects of lesion/stenosis C of vessel 302 based on a percutaneous coronary intervention (PCI), which may include angioplasty, stenting, and/or other suitable intervention to treat lesion/stenosis C of vessel 302. In that regard, FIG. 13 also provides a bar graph 370 that depicts the change in pressure ratio values that also removes the effects of lesion/stenosis C of vessel 302. In particular, bar graph 370 is similar to bar graph 320 of FIG. 10, but the region 326 associated with lesion/stenosis C of bar graph 320 has been replaced with region 372 representative of lesion/stenosis C being treated. In particular, treated lesion/stenosis C is shown to cause no change in the pressure ratio. Finally, FIG. 13 also provides an intensity map visual representation 380 for the vessel 302 based on the estimated pressure ratio values associated with the treatment of lesion/stenosis C. As shown, the proposed treatment of lesion/stenosis C causes estimated pressure ratio along the full length of the vessel 302 to be above the threshold value of 0.90. Thus, the entire intensity map is colored or otherwise visualized to indicate that the pressure ratio is above the threshold value as there are no portions below the threshold value. In the illustrated embodiment, a green color is utilized to represent values above the threshold value. In addition to the graphical visualizations of the proposed treatment options as shown in FIG. 13, the proposed treatment options can also be visualized on the angiographic or other image of the vessel. For example, an angiographic image of the vessel 302 can be annotated to include a proposed stent 392 across lesion/stenosis C. Further, it should be noted that the various other visualization techniques utilized to convey the information of the pressure measurements of the vessel 302 may also be applied to the estimated pressure measurements for the simulated treatment options, including various combinations of those visualization techniques as described above.

Additional diagnostic techniques can be utilized to assess the vessel, including those described in U.S. patent application Ser. No. 14/335,603, filed Jul. 18, 2014 published as U.S. Patent Application Publication No. 2015/0025330, published on Jan. 22, 2015 and titled "Devices, Systems, and Methods for Assessment of Vessels," PCT Patent Application No. PCT/US2012/051566, filed Aug. 20, 2012, published as WO2013/028612 published on Feb. 28, 2013 and titled "Devices, Systems, and Methods for Visually Depicting a Vessel and Evaluating Treatment Options," and U.S. patent application Ser. No. 13/978,697, filed Jul. 8, 2013, published as 2013/0345574 on Dec. 26, 2013 and titled "Apparatus and Method of Characterising a Narrowing in a Fluid Filled Tube," each of which is hereby incorporated by reference in its entirety.

Referring now to FIGS. 14a-16c, shown therein are aspects of methods and associated systems for treating a vessel according to the present disclosure and, in particular, aspects of guiding placement of one or more treatment devices associated with a treatment option. In that regard, the information from performing one or more of the diagnostic and/or evaluation techniques described above can be utilized to annotate a live image of the vessel based on a current position of one or more treatment devices and the expected results of applying the treatment device(s). The expected results of applying the treatment device(s) can include an immediate expected result, a future expected result (e.g., after a predetermined amount time, such as minutes, hours, days, weeks, months, years, etc.), and/or combinations thereof. In some instances, the expected results are estimated based on empirical data for patients having similar characteristics to the current patient.

The one or more treatment devices can include one or more of an angioplasty device (e.g., balloon catheter), ablation device (e.g., rf, laser, cryoablation, or other suitable device), drug-eluting devices (e.g., balloons, stents, etc.), stents, valves, and/or other suitable treatment devices. In that regard, the treatment devices can include devices that are placed within the vessel only during a treatment procedure (e.g., catheters, guide wires, probes, etc.), devices placed within the vessel temporarily, but for a time period that extends beyond the treatment procedure (e.g., devices/materials that dissolve and/or are absorbed over time, or devices/materials that are removed after a predetermined amount of time following the initial treatment procedure), and/or devices permanently implanted within the vessel. For the sake of clarity, the following discussion will utilize a stent as an exemplary treatment device. However, it is understood that similar approaches may be utilized for any of the treatment devices described in the present disclosure.

Figure 14A:
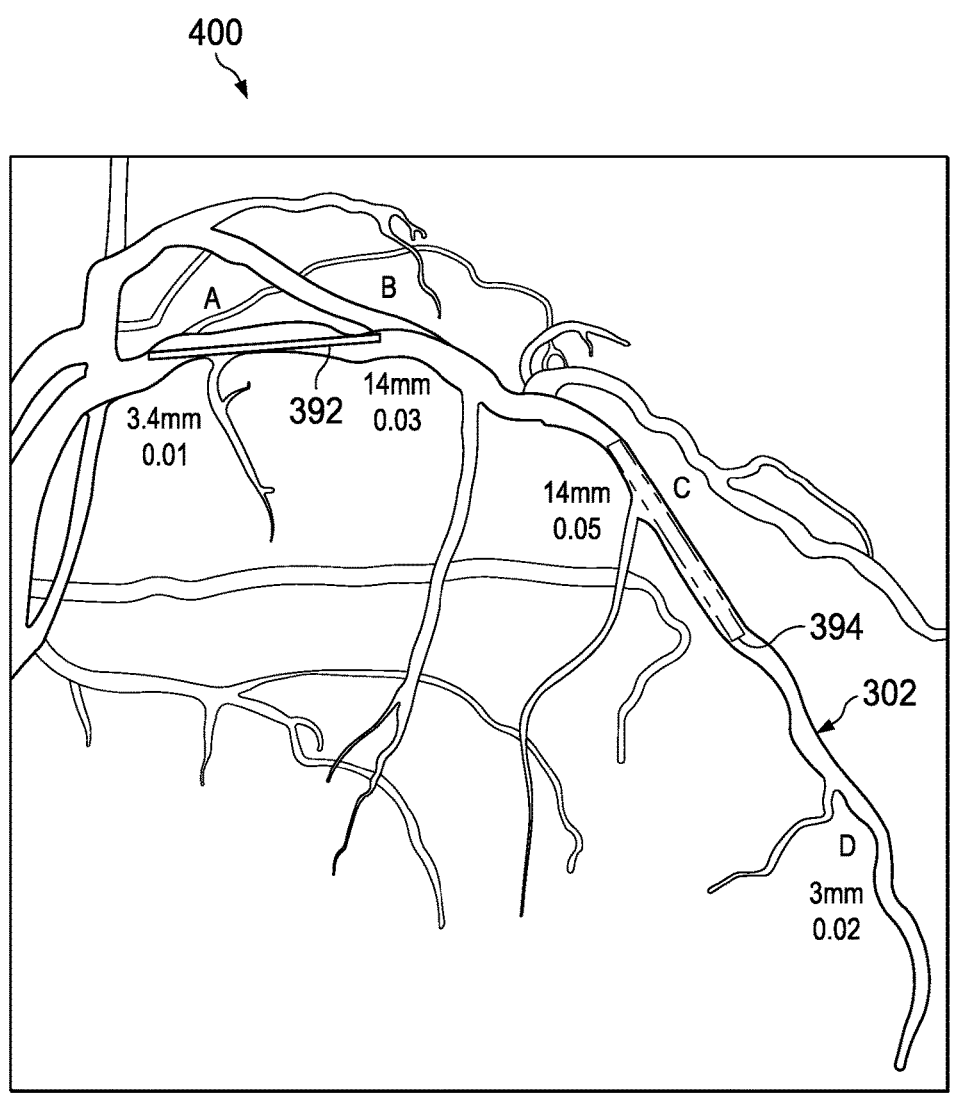
FIGS. 14*a*-14*c* illustrate annotated versions of an angiographic image to guide placement of a treatment device according to an embodiment of the present disclosure. In particular.
Figure 14B:
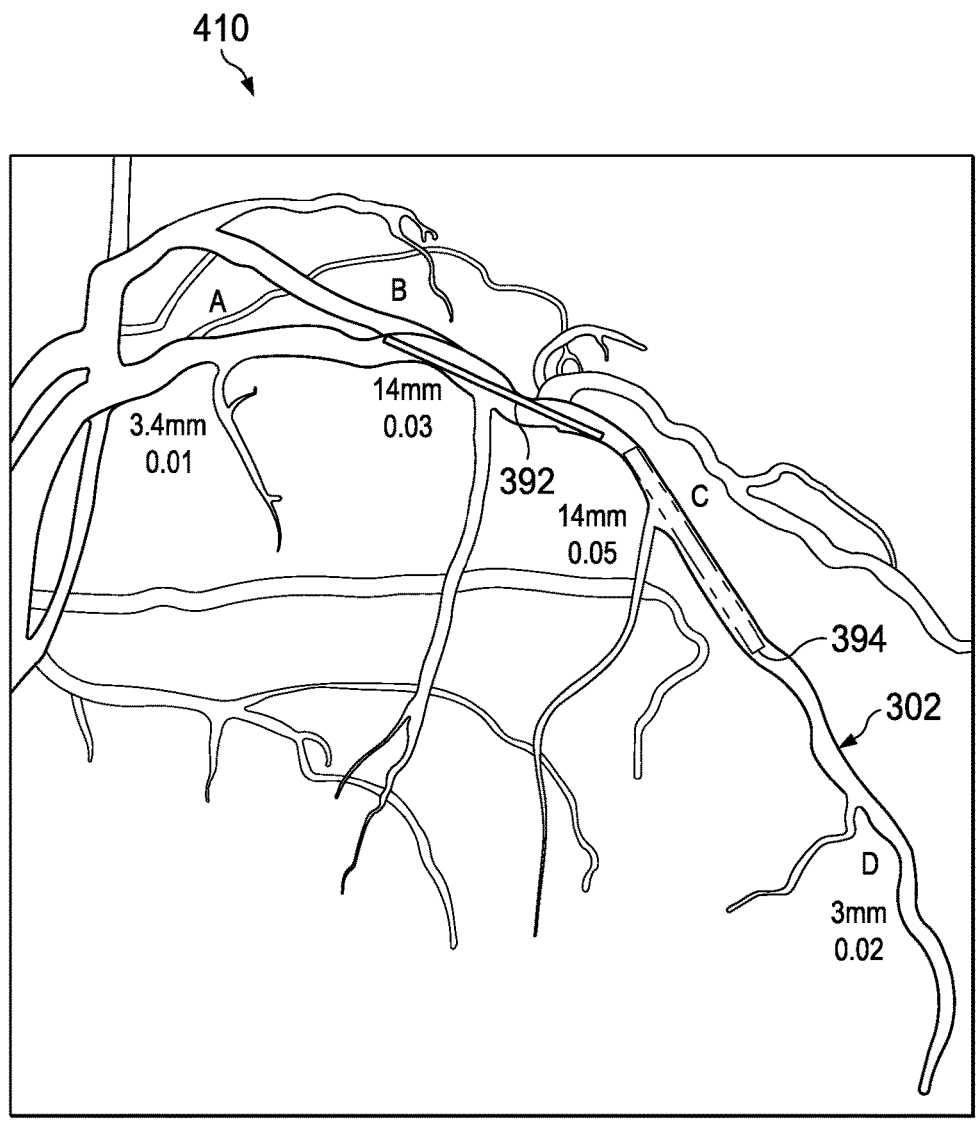
Figure 14C:
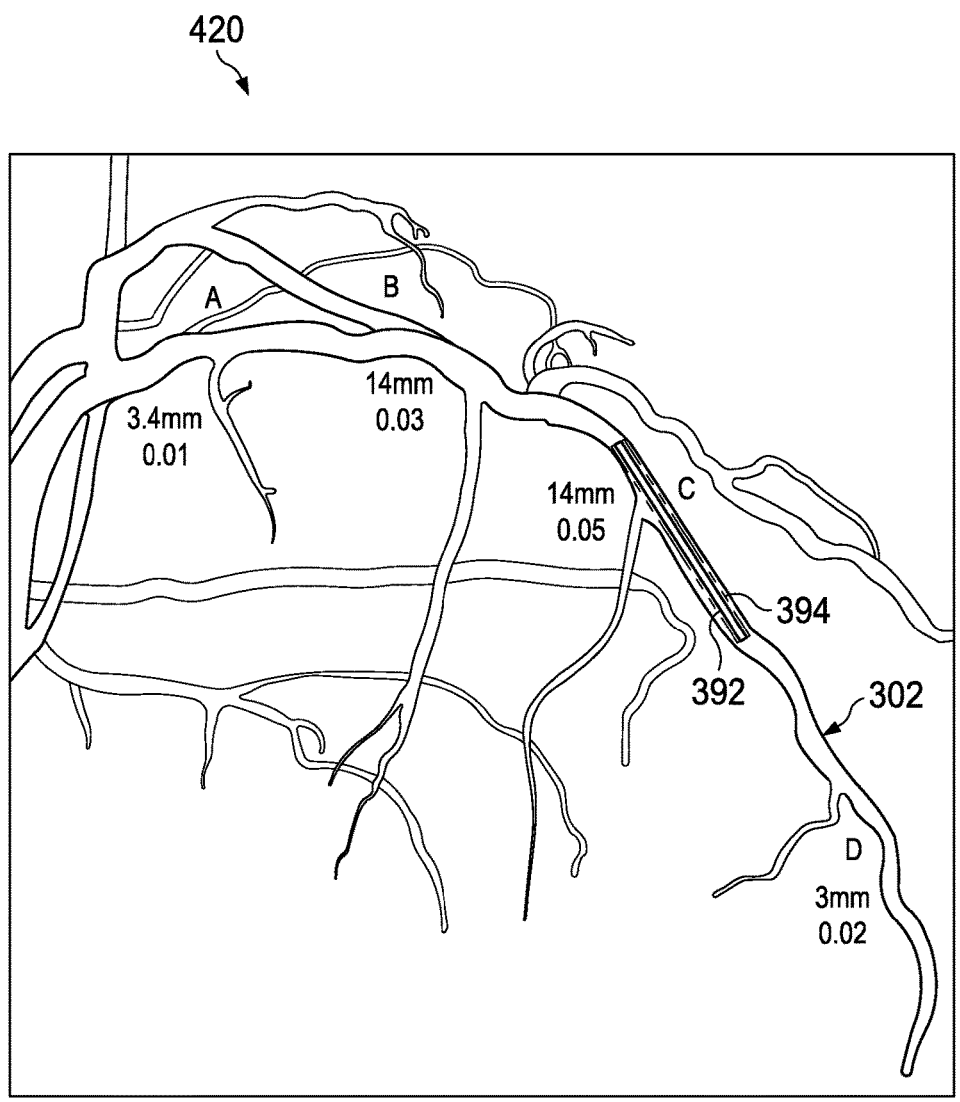

Referring now to FIGS. 14a-14c, shown therein is a series of images 400, 410, and 420 illustrating an aspect of guiding placement of a treatment device 392 within the vessel 302 according to the present disclosure. In particular, each of FIGS. 14a-14c shows the position of the treatment device 392 relative to a desired deployment location 394 for the treatment device. In that regard, the desired deployment location 394 is identified as the optimal placement for the treatment device 392 based on or more of the diagnostic and/or evaluation techniques described above in some instances.

As shown in FIGS. 14a-14c, the treatment device 392 is guided through the vessel 302 until it reaches the desired deployment location 394. For example, FIG. 14a shows the treatment device 392 extending across lesion A toward lesion B. In that regard, the image 400 includes information about each of the lesions A, B, C, and D that may be useful to the physician in determining where to deploy the stent. In particular, the illustrated embodiment provides the length of each lesion and the lesion's effect on the overall pressure ratio, FFR, or iFR value for the vessel 302. For example, in the illustrated embodiment lesion A has a length of 3.4 mm and an effect of 0.01 on the iFR value, lesion B has a length of 14 mm and an effect of 0.03 on the iFR value, lesion C has a length of 14 mm and an effect of 0.05 on the iFR value, and lesion D has a length of 3 mm and an effect of 0.02 on the iFR value. FIG. 14b shows the treatment device 392 extending across lesion B towards lesion C. Finally, FIG. 14c shows the treatment device 392 extending across lesion C and in alignment with the desired deployment location 394. In that regard, the treatment device 392 is shown in an undeployed or reduced diameter configuration, while the desired deployment location 394 is representative of the treatment device 392 in a fully deployed or expanded configuration. Accordingly, in some instances the size of the treatment device 392 relative to the visual representation of the desired deployment location 394 can provide an indication to the physician as to whether the treatment device 392 has been fully expanded/deployed as desired.

Figure 15C:
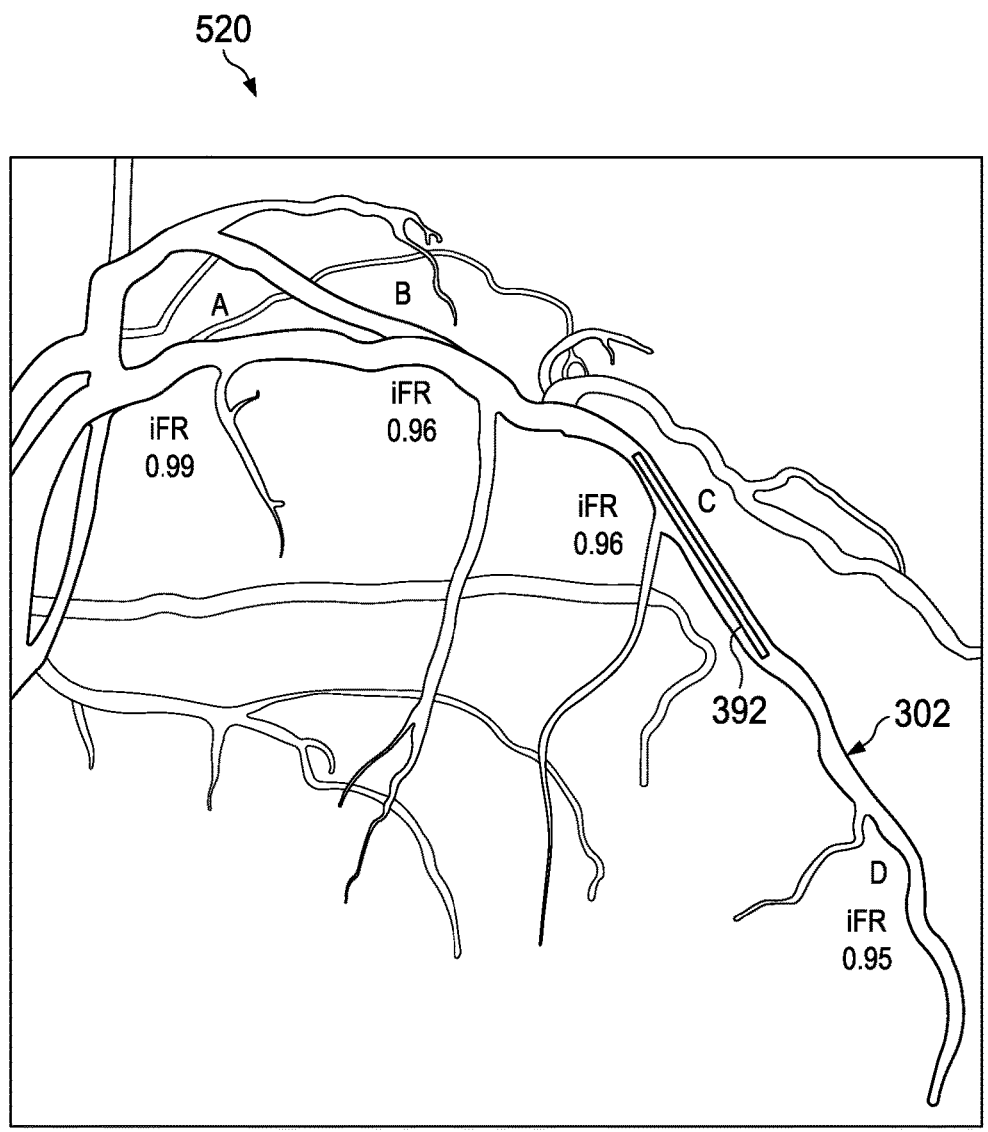
Figure 16A:
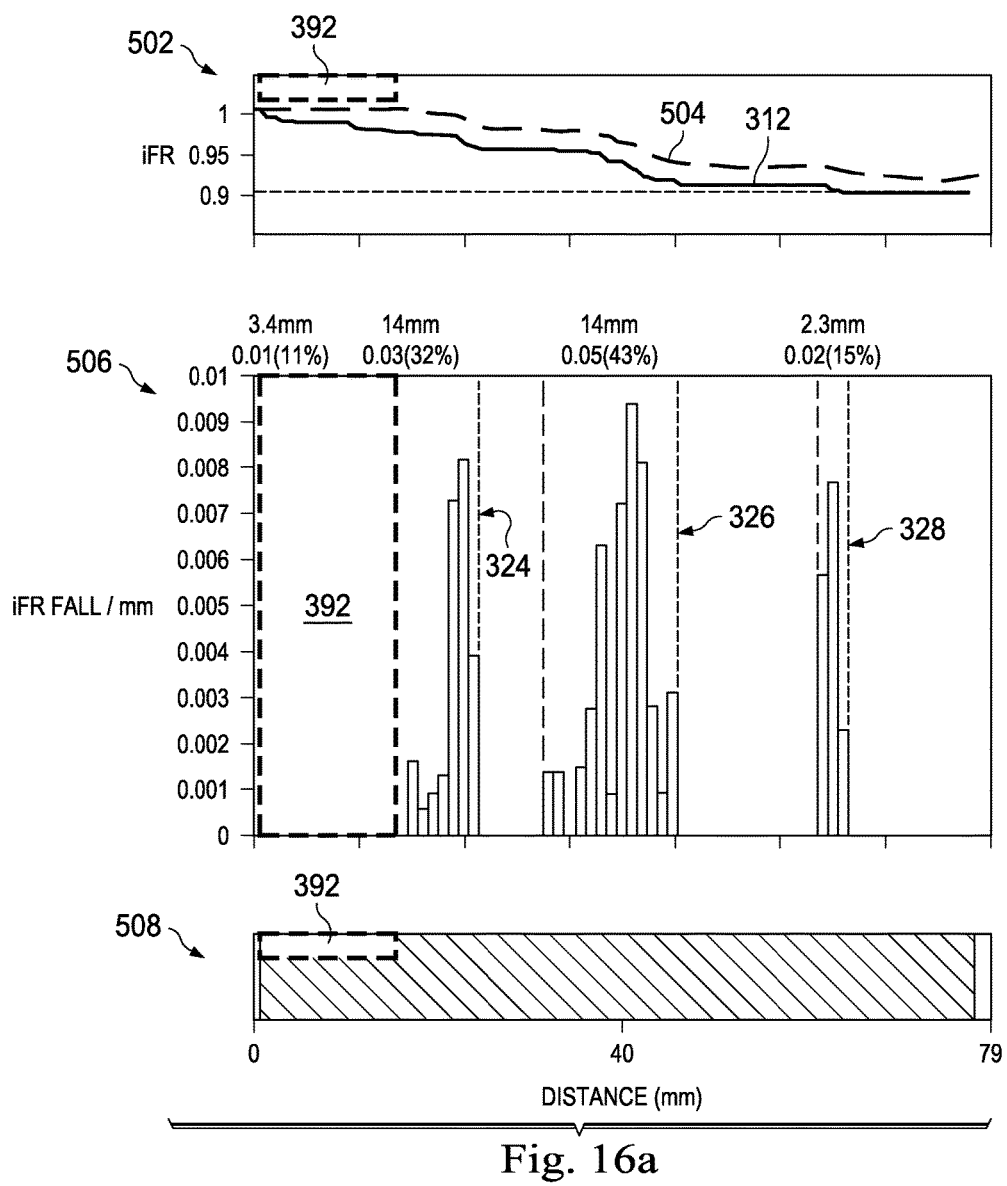
Figure 16B:
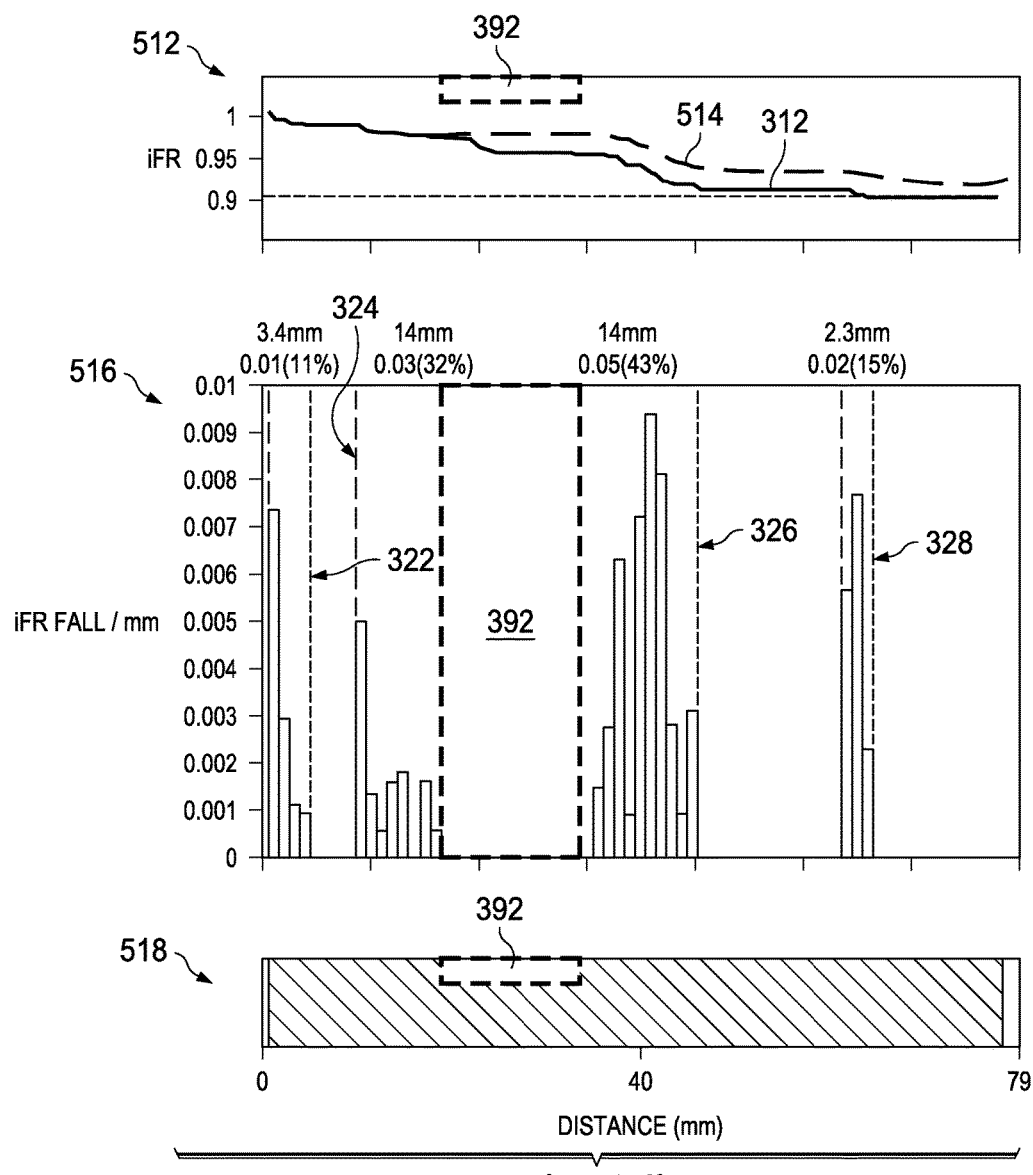
Figure 16C:
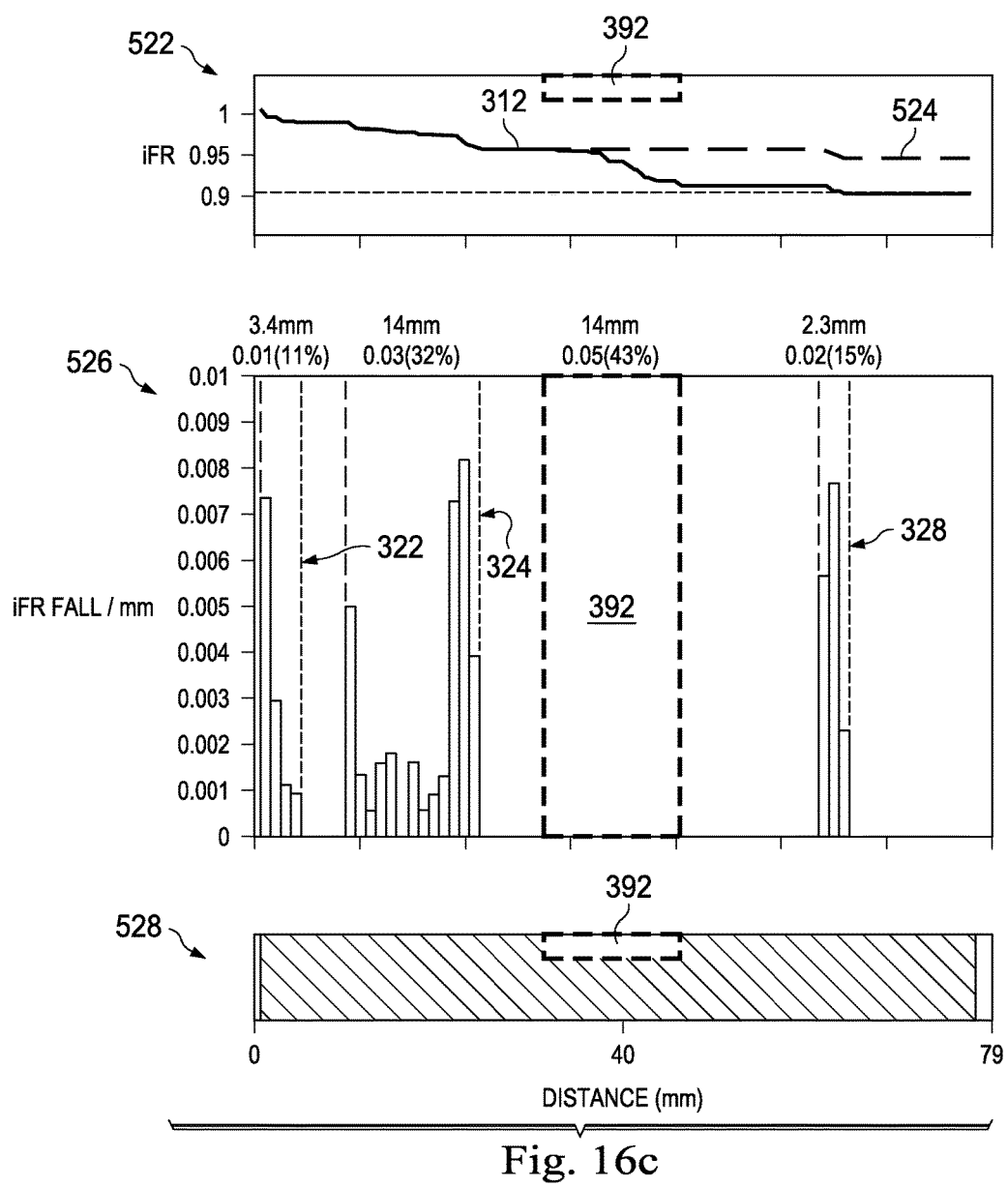
FIG. 16*c* shows the treatment device at a third position within the vessel.

Referring now to FIGS. 15a-15c, shown therein is a series of images 500, 510, and 520 illustrating an aspect of guiding placement of the treatment device 392 within the vessel 302 according to the present disclosure. In particular, each of FIGS. 15a-15c shows the current position of the treatment device 392 within the vessel 302 and the corresponding iFR values along the vessel if the treatment device 392 were to be deployed in the current position. For example, FIG. 15a shows the treatment device 392 extending across lesion A toward lesion B. With the treatment device in that position, the image 500 displays the corresponding iFR values across each of the A, B, C, and D based on the expected effect of deploying the treatment device 392 in that location. Accordingly, in the position of FIG. 15a, the expected iFR values would be as follows, 1.00 at lesion A, 0.99 at lesion B, 0.94 at lesion C, and 0.92 at lesion D. FIG. 15b shows the treatment device 392 extending across lesion B towards lesion C. As shown, the iFR values across the lesions A, B, C, and D have been updated based on the new position of the treatment device. In the position of FIG. 15b, the expected iFR values would be as follows, 0.99 at lesion A, 0.97 at lesion B, 0.93 at lesion C, and 0.92 at lesion D. Finally, FIG. 15c shows the treatment device 392 extending across lesion C. Again, the iFR values across the lesions A, B, C, and D have been updated based on the new position of the treatment device. In the position of FIG. 15c, the expected iFR values would be as follows, 0.99 at lesion A, 0.96 at lesion B, 0.96 at lesion C, and 0.95 at lesion D. Accordingly, deploying the treatment device 392 in the position of FIG. 15c results in the lowest total drop in iFR across the vessel (0.95 versus 0.92 in the previous two positions). In this manner, the treatment device 392 can be moved through the vessel 302 until the estimated iFR values are optimized. After deployment of the treatment device 392 actual iFR value calculations can be made to ensure that the expected effect of the treatment has been obtained. For example, in some instances an effect less than expected can be an indication that the treatment device was not fully deployed and/or that the treatment plan needs to otherwise be modified. In that regard, in some instances a visual representation of a desired deployment location, including an expected expanded profile of the treatment device, as described in the context of FIGS. 14a-14c can be provided in combination with the other guiding features of FIGS. 15a-15c.

Referring now to FIGS. 16a-16c, shown therein are visual depictions of a profile of the vessel that simulate deployment of the treatment device at the first, second, and third locations depicted in FIGS. 15a-15c. In particular, FIG. 16a provides visual depictions of a profile of the vessel 302 with the treatment device 392 at the first position within the vessel shown by FIG. 15a, FIG. 16b provides visual depictions of a profile of the vessel 302 with the treatment device 392 at the second position within the vessel shown by FIG. 15b, and FIG. 16c provides visual depictions of a profile of the vessel 302 with the treatment device 392 at the third position within the vessel shown by FIG. 15c. In that regard, the visual depictions in FIGS. 16a-16c are similar to the visual depictions provided in FIGS. 10 and 13 above, but modified to represent the expected effect of deployment of the treatment device 392 at the respective position.

Referring initially to FIG. 16a, shown therein is a graph 502 that includes a plot 504 representative of simulated pressure ratio value calculations based on deploying the treatment device 392 within the vessel 302 at the location represented in FIG. 15a along with the plot 312 of the original pressure ratio value calculations shown in FIG. 10. In that regard, the plot 504 is based upon removing the effects of lesion/stenosis of vessel 302 in accordance with the expected effects of the deploying particular treatment device 392 at the current location. FIG. 16a also provides a bar graph 506 and an intensity map 508 that similarly depict the change in pressure ratio values based upon removing the effects of lesion/stenosis of vessel 302 in accordance with the expected effects of deploying the particular treatment device 392 at the current location. As shown, each of the graph 502, bar graph 506, and intensity map 508 includes a visual representation of the relative location of the treatment device 392 along the length of the vessel to illustrate which lesions/stenoses of the vessel (and their corresponding adverse effects) will be treated by deploying the treatment device 392 at the current location.

FIG. 16b similarly provides a graph 512 that includes a plot 514 representative of simulated pressure ratio value calculations based on deploying the treatment device 392 within the vessel 302 at the location represented in FIG. 15b along with the plot 312 of the original pressure ratio value calculations shown in FIG. 10. In that regard, the plot 514 is based upon removing the effects of lesion/stenosis of vessel 302 in accordance with the expected effects of the deploying particular treatment device 392 at the current location, illustrated in FIG. 15b. FIG. 16b also provides a bar graph 516 and an intensity map 518 that similarly depict the change in pressure ratio values based upon removing the effects of lesion/stenosis of vessel 302 in accordance with the expected effects of deploying the particular treatment device 392 at the location shown in FIG. 15b.

Finally, FIG. 16c provides a graph 522 that includes a plot 524 representative of simulated pressure ratio value calculations based on deploying the treatment device 392 within the vessel 302 at the location represented in FIG. 15c along with the plot 312 of the original pressure ratio value calculations shown in FIG. 10. In that regard, the plot 524 is based upon removing the effects of lesion/stenosis of vessel 302 in accordance with the expected effects of the deploying particular treatment device 392 at the current location, illustrated in FIG. 15c. FIG. 16c also provides a bar graph 526 and an intensity map 528 that similarly depict the change in pressure ratio values based upon removing the effects of lesion/stenosis of vessel 302 in accordance with the expected effects of deploying the particular treatment device 392 at the location shown in FIG. 15c.

One or more of the graphs 502, 512, 522, bar graphs 506, 516, 526, or the intensity maps 508, 518, 528 may be shown overlaid onto and/or shown adjacent to the images of FIGS. 14a-15c to further guide the placement of the treatment device 392 within the vessel 302. Further, while the images 400, 410, 420, 500, 510, and 520 are shown as being representative of live angiography or fluoroscopy images, it is understood that in other instances other types of extravascular or intravascular images are utilized in a similar manner. Further, in some instances a combination of images, intravascular and/or extravascular, are provided simultaneously. When multiple images are provided, one or more of the images may be annotated or include visualizations as described above to guide the positioning of one or more treatment devices within the vessel 302.

Further, it is understood that multiple treatment devices may be guided into place within the vessel 302 using the techniques described above. In that regard, the treatment devices may be guided in to place serially (i.e., one at a time) such that the visualizations on the images of the vessel take into account any previously deployed treatment devices when positioning the later treatment device(s). Further, multiple treatment devices may be guided in to place simultaneously (i.e., two or more at the same time) such that the visualizations on the images of the vessel take into account the relative locations of each of the treatment devices and the associated expected effectiveness of each treatment device at the respective locations to provide a cumulative and/or collective expected effectiveness of deploying the treatment devices at those locations.

In some instances, the pre-treatment or diagnostic pressure measurement information, such as shown in FIGS. 10-12, is compared to corresponding post-treatment pressure measurement information. In that regard, the difference between the pre-treatment and post-treatment measurement information will indicate whether the treatment achieved the desired functional gain of allowing the blood to flow through the vessel. Likewise, the post-treatment pressure measurement information can be compared to the estimated pressure measurement information for the simulated treatment, such as shown in FIG. 13. In that regard, the differences between the estimated measurement information and the actual post-treatment measurement information will provide an indication of the accuracy of the estimated measurement information for the simulated treatment. In that regard, in some instances the differences between estimated measurement information and actual post-treatment measurements are stored by the system and utilized to modify future estimated measurement information for similar treatment options. In some instances, the system is configured to automatically link or coordinate the pressure data and corresponding vessel locations between the pre-treatment, simulated treatment, and/or post-treatment measurement information.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of treating a vessel of a patient, comprising:
   obtaining pressure measurements from a first instrument and a second instrument positioned within a vessel of a patient during a diagnostic procedure where the second instrument is moved longitudinally through the vessel from a first position to a second position and the first instrument remains stationary within the vessel;
   identifying a desired treatment location of the vessel based on the pressure measurements; and
   outputting, to a user display, a graphical representation comprising an image of the vessel and an indicator of one or more treatment devices at the desired treatment location of the vessel, wherein the image of the vessel comprises a length of the vessel, and wherein the indicator is overlaid on the image of the vessel such that the indicator extends lengthwise along the length of the vessel in the graphical representation.

2. The method of claim 1, wherein the image of the vessel is an intravascular image.

3. The method of claim 2, wherein the intravascular image is at least one of an intravascular ultrasound (IVUS) image or an optical coherence tomography (OCT) image.

4. The method of claim 1, wherein the image of the vessel is an extravascular image.

5. The method of claim 4, wherein the extravascular image is at least one of a two dimensional angiographic image, a three dimensional angiographic image, or a computed tomography angiographic (CTA) image.

6. The method of claim 1, wherein the step of identifying includes outputting the image of the vessel on the user display, the image including diagnostic visualizations based on the pressure measurements.

7. The method of claim 6, wherein the diagnostic visualizations include an intensity map based on changes in a pressure ratio of the pressure measurements from the first instrument and second instrument.

8. The method of claim 6, wherein the diagnostic visualizations include a graph of at least one of:
a pressure ratio of the pressure measurements from the first instrument and second instrument; or
a gradient of a pressure ratio of the pressure measurements from the first instrument and second instrument.

9. The method of claim 8, wherein the graph is at least one of scaled, rotated, or mirror imaged to align proximal and distal portions of the graph with corresponding proximal and distal portions of the vessel as depicted in the image of the vessel.

10. The method of claim 6, wherein the diagnostic visualizations include numerical values of a pressure ratio of the pressure measurements from the first instrument and second instrument.

11. The method of claim 6, wherein the diagnostic visualizations include markings representative of a pressure ratio of the pressure measurements from the first instrument and second instrument.

12. The method of claim 1, wherein the step of identifying includes modifying the image of the vessel to simulate one or more treatment options.

13. The method of claim 12, wherein the modifying the image of the vessel to simulate one or more treatment options includes:
modifying the image of the vessel to simulate a first treatment option;
modifying the image of the vessel to simulate a second treatment option; and
evaluating the modified images of the vessel to select either the first treatment option or the second treatment option as a desired treatment option.

14. The method of claim 12, wherein the one or more treatment options are selected from the group consisting of performing angioplasty, deploying one or more stents, applying a pharmaceutical agent, and combinations thereof.

15. The method of claim 1, wherein the indicator is representative of at least one of a stent or a balloon placed at the desired treatment location.

16. The method of claim 1, wherein the indicator is oriented within the image of the vessel based on a shape of the vessel at the desired treatment location.

17. The method of claim 1, further comprising:
identifying a treatment option based on the pressure measurements; and
performing the treatment option, wherein the performing includes guiding placement of the one or more treatment devices, using the image of the vessel and the indicator at the desired treatment location of the vessel, by moving the one or more treatment devices to the desired treatment location based on the indicator.

18. The method of claim 17, wherein the guiding placement of the one or more treatment devices to the desired treatment location includes outputting to the user display a current location of the one or more treatment devices within the vessel along with the desired treatment location of the vessel based on the treatment option.

19. The method of claim 17, wherein the guiding placement of the one or more treatment devices to the desired treatment location includes outputting to the user display a current location of the one or more treatment devices within the vessel along with an estimated treatment value associated with deploying the one or more treatment devices at the current location.

20. The method of claim 19, wherein the estimated treatment value is a visual representation of an expected pressure ratio of deploying the one or more treatment devices at the current location relative to the pressure measurements.

21. The method of claim 20, wherein the estimated treatment value is a color indicating the expected pressure ratio value.

22. The method of claim 19, wherein the estimated treatment value includes multiple estimated treatment values, wherein the multiple estimated treatment values are provided along a length of the vessel corresponding to a placement of the one or more treatment devices.

23. The method of claim 1, wherein the indicator comprises a first dimension and a second dimension within the image of the vessel in the graphical representation.

24. The method of claim 1, wherein the desired treatment location comprises a portion of the length of the vessel, and wherein the indicator spans the portion of the length of the vessel.

25. The method of claim 1, wherein the desired treatment location is a proposed treatment location identified before the one or more treatment devices are deployed within the vessel.

26. The method of claim 1, wherein the desired treatment location corresponds to a blockage of the vessel that is identified using the pressure measurements.

27. A system for treating a vessel of a patient, comprising:
a first instrument sized and shaped for introduction into the vessel of the patient;
a processing system in communication with the first instrument and a second instrument sized and shaped for introduction into the vessel of the patient, the processing system configured to:
obtain pressure measurements from the first instrument and second instrument while the second instrument is moved longitudinally through the vessel of the patient from a first position to a second position while the first instrument is maintained in a fixed longitudinal position with respect to the vessel;
identify a desired treatment location based on the pressure measurements; and
output, to a user display, a graphical representation comprising an image of the vessel and an indicator of one or more treatment devices at the desired treatment location of the vessel, wherein the image of the vessel comprises a length of the vessel, and wherein the indicator is overlaid on the image of the vessel such that the indicator extends lengthwise along a length of the vessel in the graphical representation.

28. The system of claim 27, wherein the processing system is configured to guide placement of the one or more treatment devices by outputting to the user display a current location of the one or more treatment devices overlaid on the image of the vessel.

* * * * *